(12) United States Patent
Crawford et al.

(10) Patent No.: US 8,927,807 B2
(45) Date of Patent: Jan. 6, 2015

(54) NITRATE-RESPONSIVE PROMOTER

(75) Inventors: Nigel Crawford, San Diego, CA (US); Rongchen Wang, San Diego, CA (US); Peizhu Guan, San Diego, CA (US); Mingsheng Chen, Beijing (CN)

(73) Assignee: The Regents of the University of California, Oakland, CA (US)

( * ) Notice: Subject to any disclaimer, the term of this patent is extended or adjusted under 35 U.S.C. 154(b) by 395 days.

(21) Appl. No.: 13/392,496

(22) PCT Filed: Sep. 2, 2010

(86) PCT No.: PCT/US2010/047716
§ 371 (c)(1),
(2), (4) Date: May 7, 2012

(87) PCT Pub. No.: WO2011/028929
PCT Pub. Date: Mar. 10, 2011

(65) Prior Publication Data
US 2012/0210460 A1 Aug. 16, 2012

Related U.S. Application Data

(60) Provisional application No. 61/239,721, filed on Sep. 3, 2009.

(51) Int. Cl.
*C12N 15/82* (2006.01)
*C12N 15/00* (2006.01)
*C12N 5/04* (2006.01)
*C12N 5/10* (2006.01)
*C07H 21/04* (2006.01)
*A01H 5/00* (2006.01)
*C07K 14/415* (2006.01)

(52) U.S. Cl.
CPC .......... *C12N 15/8238* (2013.01); *C07K 14/415* (2013.01)
USPC ........ 800/278; 435/419; 435/468; 435/320.1; 800/298; 536/24.1

(58) Field of Classification Search
None
See application file for complete search history.

(56) References Cited

U.S. PATENT DOCUMENTS 6,818,807 B2   11/2004   Trolinder et al.
7,176,301 B2    2/2007   Ozawa

FOREIGN PATENT DOCUMENTS

WO      WO 02/16655 A2    2/2002

OTHER PUBLICATIONS

Fourgoux-Nicol Plant Mol Biol 40 857 1999.*
Dolferus_Plant Phys_105_1075_1994.*
Kim_Plant Mol Biol_24_105_1994.*
Donald_EMBO J_9_1717_1990.*
AC006248_2002.*
Meinkoth Wahl_Anal Biochem_138_267_1984.*
International Search Report from PCT/US2010/047716, dated Jun. 13, 2011 (4 pages).
Girin et al.; "Identification of a 150 bp *cis*-acting element of the *AtNRT2.1* promoter involved in the regulation of gene expression by the N And C status of the plant"; *Plant, Cell and Environment*; 30(11):1366-1380 (2007).
Konishi et al.; "Identification of a nitrate-responsive *cis*-element in the Arabidopsis *NIR1* promoter defines the presence of multiple *cis*-regulatory elements for nitrogen response"; *Plant Journal*; 63:269-282 (2010).
Tanaka et al.; "Nucleotide sequence of a gene for nitrite reductase from Arabidopsis thaliana"; *DNA Seq.*; 5(l):57-61 (1994).
Wang et al.; "A Genetic Screen for Nitrate Regulatory Mutants Captures the Nitrate Transporter Gene *NRT1.1*"; *Plant Physiology*; 151:472-478 (2009) Epub Jul. 24, 2009.

* cited by examiner

*Primary Examiner* — Medina A Ibrahim
*Assistant Examiner* — Russell Boggs
(74) *Attorney, Agent, or Firm* — Kilpatrick Townsend & Stockton LLP

(57) ABSTRACT

The present invention provides methods for screening for nitrate-regulated promoter and enhancer elements in plant cells. The present invention also provides expression cassettes that contain nitrate-regulated promoters operably linked to heterologous polynucleotide sequences. The expression cassettes of the present invention are useful for expressing polypeptides, proteins and nucleic acid molecules in plant cells treated with nitrates and nitrites.

23 Claims, 17 Drawing Sheets

NITRATE-RESPONSIVE PROMOTER

CROSS-REFERENCE TO RELATED APPLICATIONS

This application is the U.S. National Stage entry of International Application No. PCT/US2010/047716, filed Sep. 2, 2012, which claims benefit of U.S. Provisional Application No. 61/239,721, filed Sep. 3, 2009; the contents of each are herein incorporated by reference.

STATEMENT AS TO RIGHTS TO INVENTIONS MADE UNDER FEDERALLY SPONSORED RESEARCH AND DEVELOPMENT

This invention was made with Government support under RO 1 GM40672 awarded by National Institutes of Health, and NSF IOB-051998502 awarded by the National Science Foundation. The Government has certain rights in the invention.

REFERENCE TO A SEQUENCE LISTING

This application includes a Sequence Listing as a text file named "SEQTXT_88424-832030_004610US.txt" created Feb. 23, 2012 and containing 9,094 bytes. The material contained in this text file is incorporated by reference.

BACKGROUND OF THE INVENTION

Inorganic nitrogen is a vital nutrient for plants. Plants take up and assimilate both nitrate and ammonium with nitrate being the predominant form in most agricultural soils (Crawford N M, Glass A D M, *Trends Plant Sci.*, 3: 389-395 (1998)). Nitrate is taken up by roots then transported into cells via transporters from the NRT1 and NRT2 family of nitrate transporters (Forde B G, *Biochim. Biophys. Acta*, 1465: 219-235 (2000); Tsay Y F et al., *FEBS Lett*, 581: 2290-2300 (2007)). Once inside the cell, nitrate is reduced to nitrite by nitrate reductase (NIA) then to ammonium by nitrite reductase (NiR). Ammonium is then assimilated into amino acids.

Nitrate has two functions in plants; it serves as a nutrient and as a signal. Plants undergo many physiological and developmental changes when they are exposed to nitrate. One of the fastest responses is reprogramming of the plant transcriptome. When plants are exposed to nitrate, genes in the nitrate assimilation pathway (NRT, NIA, NiR) are induced within minutes (Wang R et al., *Plant Physiol.*, 132: 556-567 (2003); Scheible W R et al., *Plant Physiol.*, 136: 21013(2003483-2499 (2004); Wang R et al., *Plant Physiol.*, 145: 1735-1745 (2007)). Other genes, which are involved in carbon and energy metabolism that support nitrate assimilation, are also rapidly induced (Stitt M, *Curr. Opin. Plant Biol.*, 2: 178-186 (2006) (1999); Wang R et al., *Plant Cell*, 12: 1491-1509 (2000); Stitt M et al., *J Exp Bot.*, 53: 959-970 (2002); Wang R et al., *Plant Physiol.*, 132: 556-567 (2003); Scheible W R et al., *Plant Physiol.*, 136: 2483-2499 (2004); Wang R et al., *Plant Physiol.*, 136: 2512-2522 (2004); Fritz C et al., *Plant J*, 46: 533-548 (2006)). Transcriptome analyses have shown that over 1500 genes are rapidly induced or repressed by nitrate and that the processes of pentose phosphate oxidation, glycolysis, trehalose synthesis, nitrogen and amino acid metabolism are most affected (Wang R et al., *Plant Physiol.*, 132: 556-567 (2003); Scheible W R et al., *Plant Physiol.*, 136: 2483-2499 (2004); Wang R et al., *Plant Physiol.*, 136: 2512-2522 (2004); Gutierrez R A et al., *J Exp Bot*, 58: 2359-2367 (2007); Wang R et al., *Plant Physiol.*, 145: 1735-1745 (2007)). These rapid transcriptome responses provide the basis for the longer-term responses that direct root growth, development and architecture, root to shoot ratios and germination rates (Forde B G, *Annu. Rev. Plant Biol.*, 53: 203-224 (2002); Alboresi A et al., *Plant Cell Environ*, 28: 500-512 (2005); Filleur S et al., *Biochem Soc Trans*, 33: 283-286 (2005); Forde B G, Walch-Liu P, *Plant Cell Environ.*, 32: 682-693 (2009)).

Even though nitrate responses have been reported for plants for over forty years, the first biochemical response being reported in 1957 (Tang P S, Wu H Y, *Nature*, 179: 1355-1356 (1957)), the regulatory genes that mediate these responses are just now being identified. So far, several potential transcription factors, two kinases and a transceptor have been linked to nitrate regulation (Krouk G et al., *Curr Opin Plant Biol.*, 2010/01/23: 10.1016/j.pbi.2009.1012.1003 (2010)). The ANR1 MADS box transcription factor, which is induced by N deprivation, controls lateral root branching in response to nitrate (Zhang H M, Forde B G, *Science*, 279: 407-409 (1998); Gan Y et al., *Planta*, 222: 730-742 (2005)). The NIN-like gene NLP7, encoding a potential bZIP DNA binding protein, was identified through its sequence similarity to the nitrate regulatory gene NIT2 in *Chlamydomonas* (Camargo A et al., *Plant Cell*, 19: 3491-3503 (2007)) and functions in nitrate induction of several nitrate assimilatory genes (Castaings L et al., *Plant J*, 57: 426-435 (2009)). Three members of the Lateral Organ Boundary Domain gene family (LBD37, 38 and 39) were identified as nitrate-inducible genes and shown to be repressors of anthocyanin biosynthetic and nitrate assimilatory genes (Rubin G et al., *Plant Cell*, 21: 3567-3584 (2009)). Two kinase genes CIPK8 and CIPK23 were identified as nitrate-inducible genes. Mutations in CIPK8 result reduced gene induction at high but not low nitrate concentrations (Hu H C et al., *Plant J*, 57: 264-278 (2009)) while mutations in CIPK23 increase gene induction at low nitrate concentrations, indicating that these kinases selectively target different phases (i.e. high affinity versus low affinity phases) of the nitrate response. Interestingly, CIPK23 phosphorylates the nitrate transporter NRT1.1 (CHL1, (Tsay Y-F et al., *Cell*, 72: 705-713 (1993))), which has been shown to act as a nitrate regulator/sensor (Ho C H et al., *Cell*, 138: 1184-1194 (2009); Wang R et al., *Plant Physiol.*, 151: 472-478 (2009); Krouk G et al., *Curr Opin Plant Biol.*, 2010/01/23: 10.1016/j.pbi.2009.1012.1003 (2010)).

Even though several transcription factors have been identified, little is known about the cis-acting regulatory elements in nitrate-regulated promoters. One reason for the slow progress in identifying specific elements within nitrate enhancers is that no transient system has been reported in higher plants for rapid testing of nitrate-responsive promoters.

DEFINITIONS

The phrase "nucleic acid" or "polynucleotide sequence" refers to a single or double-stranded polymer of deoxyribonucleotide or ribonucleotide bases read from the 5' to the 3' end. Nucleic acids may also include modified nucleotides that permit correct read through by a polymerase and do not alter expression of a polypeptide encoded by that nucleic acid.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

The term "promoter" refers to a region or sequence determinants located upstream or downstream from the start of transcription and which are involved in recognition and binding of RNA polymerase and other proteins to initiate transcription. A "plant promoter" is a promoter capable of initiating transcription in plant cells. Such promoters need not be of plant origin, for example, promoters derived from plant viruses, such as the CaMV35S promoter, can be used in the present invention.

As used herein, the terms "upstream" and "downstream" refer to the relative location of nucleic acid sequences, such as DNA and RNA, to each other, and are well understood in the art. "Upstream" refers to the region of the nucleic acid sequence towards the 5' end of the single stranded nucleic acid molecule, and "downstream" refers to the region of the nucleic acid sequence towards the 3' end of the single stranded nucleic acid molecule. The terms 5' and 3' refer to location of the carbon atoms on the deoxyribose (or ribose) rings of nucleic acid molecules. In reference to promoters and expression cassettes disclosed herein, "downstream" (or 3') refers to the direction of transcription by RNA polymerase, such that the newly synthesized strand is transcribed in the 5' to 3' direction, whereas "upstream" (or 5') refers to the direction from which the RNA polymerase has come, such that the copied template strand is in the 3' to 5' orientation.

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous.

The phrase "host cell" refers to a cell from any organism. Exemplary host cells are derived from plants, bacteria, yeast, fungi, insects or other animals. Methods for introducing polynucleotide sequences into various types of host cells are well known in the art.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from any naturally occurring allelic variants.

The term "minimal promoter activity" refers to the ability of a polynucleotide sequence to initiate transcription of an operably linked polynucleotide. Typically, minimal activity will provide a low level of constitutive expression that is not inducible under most conditions or that is not cell-specific under most conditions. A minimal promoter typically comprises a TATA box and transcriptional start sequence, but does not contain additional stimulatory and repressive elements. An exemplary plant minimal promoter is positions −50 to +8 of the 35S CaMV promoter. Another exemplary plant minimal promoter is SEQ ID NO:3.

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition.

In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived. As explained below, these variants are specifically covered by this term.

Two nucleic acid sequences or polypeptides are said to be "identical" if the sequence of nucleotides or amino acid residues, respectively, in the two sequences is the same when aligned for maximum correspondence as described below. The term "complementary to" is used herein to mean that the sequence is complementary to all or a portion of a reference polynucleotide sequence.

Optimal alignment of sequences for comparison may be conducted by the local homology algorithm of Smith and Waterman *Add. APL. Math.* 2:482 (1981), by the homology alignment algorithm of Needle man and Wunsch *J. Mol. Biol.* 48:443 (1970), by the search for similarity method of Pearson and Lipman *Proc. Natl. Acad. Sci.* (*U.S.A.*) 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. Exemplary embodiments include at least: 25%, 30%, 35%, 40%, 45%, 50%, 55%, 60%, 65%, 70%, 75%, 80%, 85%, 90%, 95%, or 99%. compared to a reference sequence using the programs described herein; preferably BLAST using standard parameters.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. or 65° C.

For the purposes of this disclosure, stringent conditions for hybridizations are those which include at least one wash in 0.2×SSC at 63° C. for 20 minutes, or equivalent conditions. Moderately stringent conditions include at least one wash (usually 2) in 0.2×SSC at a temperature of at least about 50° C., usually about 55° C., for 20 minutes, or equivalent conditions.

The term "isolated", when applied to a nucleic acid or protein, denotes that the nucleic acid or protein is essentially free of other cellular components with which it is associated in the natural state. Purity and homogeneity are typically determined using analytical chemistry techniques such as polyacrylamide gel electrophoresis or high performance liquid chromatography. A protein which is the predominant species present in a preparation is substantially purified. An isolated gene is separated from open reading frames which flank the gene and encode a protein other than the gene of interest.

BRIEF SUMMARY OF THE INVENTION

The present invention provides nitrate inducible promoters that are useful for expressing heterologous polynucleotides in plant cells exposed to nitrate. Accordingly, the present invention provides a polynucleotide comprising an expression cassette having a nitrate-regulated promoter. In some embodiments, the expression cassette comprises a promoter operably linked to a heterologous polynucleotide, wherein the promoter comprises SEQ ID NO:2, SEQ ID NO:5, SEQ ID NO:7 and SEQ ID NO:8, linked to a minimal promoter sequence. In some embodiments, the promoter comprises SEQ ID NO:6, SEQ ID NO:9, or both. In some embodiments, the promoter comprises SEQ ID NO:6 and SEQ ID NO:9. In some embodiments, the promoter comprises SEQ ID NO:6 and SEQ ID NO:9 linked by a spacer sequence, wherein the spacer sequence is between 5-200 nucleotides long. In some embodiments, the promoter comprises SEQ ID NO:1 and/or SEQ ID NO:2, or one or more sequences substantially identical to SEQ ID NO:1 and/or SEQ ID NO:2 across SEQ ID NO:1 or SEQ ID NO:2's entire length, linked to a minimal promoter sequence. In some embodiments, the minimal promoter sequence comprises SEQ ID NO:3. In some embodiments, the promoter comprises SEQ ID NO:1. In some embodiments, the promoter comprises SEQ ID NO:2. In some embodiments, the promoter comprises SEQ ID NO:1 and SEQ ID NO:2, wherein SEQ ID NO:1 is upstream of SEQ ID NO:2.

In other embodiments, the promoter comprises SEQ ID NO:13, SEQ ID NO:14, or both. In some embodiments, the promoter comprises SEQ ID NO:13 and SEQ ID NO:14. In some embodiments, the promoter comprises SEQ ID NO:13 and SEQ ID NO:14 linked by a spacer sequence, wherein the spacer sequence is between 5-200 nucleotides long. In some embodiments, the promoter comprises SEQ ID NO:11 and/or SEQ ID NO:12, or one or more sequences substantially identical to SEQ ID NO:11 and/or SEQ ID NO:12 across SEQ ID NO:11 or SEQ ID NO:12's entire length, linked to a minimal promoter sequence. In some embodiments, the promoter comprises SEQ ID NO:11. In some embodiments, the promoter comprises SEQ ID NO:12. In some embodiments, the promoter comprises SEQ ID NO:11 and SEQ ID NO:12, wherein SEQ ID NO:11 is upstream of SEQ ID NO:12.

The expression cassette further comprises a heterologous polynucleotide. In one embodiment, the heterologous polynucleotide encodes a polypeptide. In another embodiment, the heterologous polynucleotide codes for an siRNA or antisense RNA.

The promoter of the present invention is nitrate responsive. In one embodiment, the promoter is nitrate responsive when introduced into a plant.

In another aspect, the invention provides a vector comprising an expression cassette comprising any of the nitrate responsive promoters described herein.

In another aspect, the present invention provides a plant, plant part, seed or plant cell comprising an expression cassette comprising any of the nitrate responsive promoters described herein.

In another aspect, the invention provides a host cell comprising an expression cassette comprising any of the nitrate responsive promoters described herein.

The present invention also provides a method of introducing an expression cassette into a cell or plant, the method comprising introducing an expression cassette comprising a nitrate responsive promoter, or a vector comprising an expression cassette comprising a nitrate responsive promoter into a cell, plant cell or plant.

In another aspect, the present invention provides a method of inducing expression of a nitrate responsive promoter in a plant, the method comprising, contacting the plant with a synthetic exogenous nitrate source, thereby inducing expression of the promoter.

DETAILED DESCRIPTION OF THE INVENTION

A. General Overview

Figure 1:
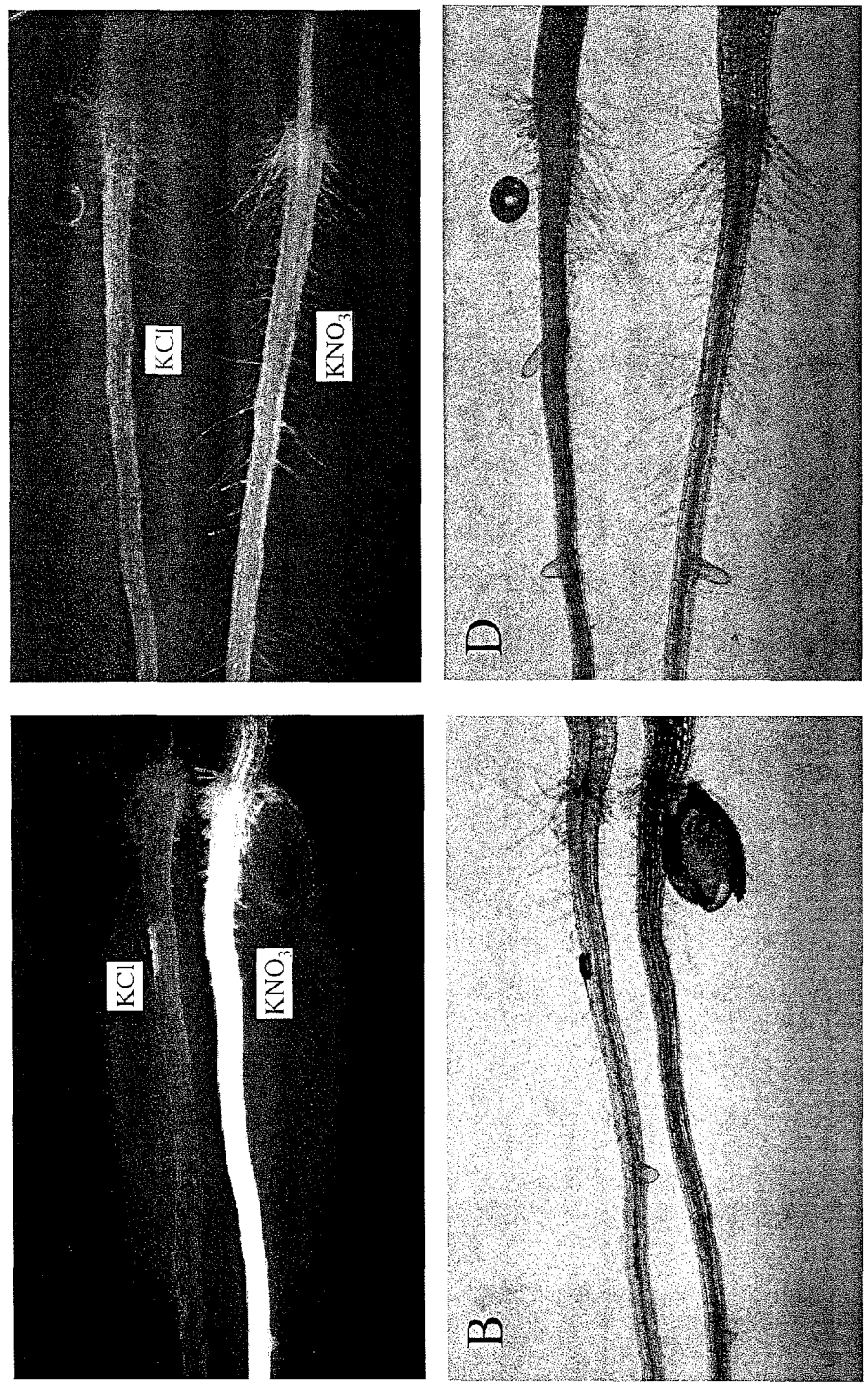
FIG. 1. Nitrate induction of NRP-YFP in wildtype and Mut21 roots. Transgenic seedlings (containing the NRP-YFP construct) grown with ammonium but no nitrate for four days were treated with either 20 mM $KNO_3$ or 20 mM KCl in the presence of 2.5 mM ammonium succinate for 16 hours. Fluorescent (Panels A & C) and visible light (panels B & D) images were captured with a fluorescent microscope to visualize YFP expression.

The present invention provides new methods of identifying and isolating plant promoters and enhancers that regulate gene expression in plant cells exposed to nitrogen fertilizers and nitrates. The invention also provides methods for identifying specific regulatory elements within nitrate responsive enhancers that regulate gene expression in response to nitrates.

The present invention also provides a nitrate inducible promoter or nitrate-regulated promoter (NRP; also referred to as a nitrate responsive promoter) that is useful in regulating the expression of endogenous and heterologous genes in plants in response to nitrates. The present invention also provides transgenic plants that comprise the NRPs of the present invention. The nitrate-regulated promoters of the invention are useful to express polypeptides and proteins when transgenic plants are fertilized with nitrates. The expressed proteins may have beneficial effects on plant growth, survival, drought tolerance, disease resistance, and pesticide and herbicide resistance, among other things. The beneficial effects of nitrate induced protein expression may be induced in the transgenic plant cells at the same time nitrogen fertilizer is applied, thereby producing two useful results from one treatment with nitrates.

In one aspect of the present invention, the NRP comprises a 1.8 kb fragment from the distal promoter region of the *Arabidopsis* nitrate reductase gene NIA1. In one embodiment, the NRP comprises an approximately 180 bp subfragment (SEQ ID NO:1; SEQ ID NO:11), isolated from the 1.8 kb NIA1 distal promoter fragment, that shows nitrate enhancer activity. The present invention also provides a polynucleotide sequence that augments the enhancer activity of the 180 bp NIA1 distal promoter fragment. In one embodiment, the polynucleotide sequence that augments the 180 bp enhancer activity comprises DNA isolated from the *Arabidopsis* NiR gene promoter. Thus, in some embodiments, the NRP comprises SEQ ID NO:2 or SEQ ID NO:12. In some embodiments, the NRP comprises SEQ ID NO:1 (or SEQ ID NO:11) and SEQ ID NO:2 (or SEQ ID NO:12). In one embodiment, SEQ ID NO:1 (or SEQ ID NO:11) is located upstream of SEQ ID NO:2 (or SEQ ID NO:12). In the above embodiments, the NRP may further comprise a Cauliflower mosaic virus (CaMV) 35S minimal promoter fragment (SEQ ID NO:3).

In one aspect of the present invention, the NRP comprises a tripartite promoter comprising three elements: an nitrate inducible enhancer, a sequence that increases the activity of the nitrate inducible enhancer, and a minimal promoter. In one embodiment of this aspect of the invention, the NRP comprises an approximately 180 bp enhancer fragment isolated from the *Arabidopsis* nitrate reductase gene NIA1 distal promoter (SEQ ID NO:1; SEQ ID NO:11); an approximately 131 bp fragment isolated from the *Arabidopsis* NiR gene promoter (SEQ ID NO:2; SEQ ID NO:12); and a CaMV 35S minimal promoter (SEQ ID NO:3). In some embodiments, the NRP comprises SEQ ID NO:15.

In another aspect, the NRP comprises cis-regulatory elements that function as nitrate enhancer elements (NEEs). In some embodiments, the cis-regulatory elements comprise HVH21, Myb-2 and/or Alfin1 transcription factor binding sites. Transcription factor binding sites were predicted using Athamap (See world wide web at athamap.de). In one embodiment, the NEEs are isolated from the 180 bp NIA1 enhancer fragment (SEQ ID NO:1; SEQ ID NO:11). In some embodiments, the NRP comprises nitrate enhancer elements comprising SEQ ID NO:5, SEQ ID NO:6, SEQ ID NO:7, SEQ ID NO:8, SEQ ID NO:9, SEQ ID NO:13, SEQ ID NO:14, SEQ ID NO:20 and/or SEQ ID NO:21. In other embodiments, the NRP comprises one or more nitrate enhancer elements selected from the group consisting of SEQ ID NOs:5, 6, 7, 8, 9, 13, 14, 20 and 21. In other embodiments, the NRP comprises various combinations of nitrate enhancer elements selected from the group consisting of SEQ ID NOs: 5, 6, 7, 8 9, 13, 14, 20 and 21. In one embodiment, the NRP comprises SEQ ID NO:6 and/or SEQ ID NO:9. In another embodiment, the NRP comprises SEQ ID NO:13 and/or SEQ ID NO:14.

In some embodiments, the NRP comprises nitrate enhancer elements operably linked to SEQ ID NO:2 (or SEQ ID NO:12) and a minimal promoter sequence. For example, in one embodiment, the NRP comprises SEQ ID NO:2 (or SEQ ID NO:12), SEQ ID NO:5, SEQ ID NO:7 (or SEQ ID NO:20), and SEQ ID NO:8 (or SEQ ID NO:21) operably linked to a minimal promoter sequence. In another embodiment, the NRP comprises SEQ ID NO:2 (or SEQ ID NO:12), SEQ ID NO:6, SEQ ID NO:7 (or SEQ ID NO:20), and SEQ ID NO:8 (or SEQ ID NO:21) operably linked to a minimal promoter sequence. In one embodiment, the NRP comprises SEQ ID NO:2 (or SEQ ID NO:12), SEQ ID NO:6 (or SEQ ID NO:13) and SEQ ID NO:9 (or SEQ ID NO:14) operably linked to a minimal promoter sequence. In some embodiments, the minimal promoter sequence is SEQ ID NO:3. In the above embodiments, the NEEs are located upstream or 5' of SEQ ID NO:2 (or SEQ ID NO:12). Generally, SEQ ID NO:2 (or SEQ ID NO:12) is located upstream of the minimal promoter sequence.

In some embodiments, the NRP comprises a 109 bp fragment (SEQ ID NO:10) isolated from the 5' end of the 180 bp enhancer fragment (SEQ ID NO:1 or SEQ ID NO:11). The 109 bp fragment (SEQ ID NO:10) provides nitrate enhancer activity substantially similar to that of the 180 bp enhancer fragment (SEQ ID NO:1 or SEQ ID NO:11). In one embodiment, the NRP comprises SEQ ID NO:10, SEQ ID NO:2 (or SEQ ID NO:12), and/or SEQ ID NO:3.

The NRP of the present invention can include promoters of lengths ranging from 2.0 Kb to 0.1 Kb, or from 2.0 Kb to less than 0.1 Kb.

One of skill in the art will appreciate that the promoter and enhancer elements disclosed herein include sequence variants that do not substantially impair the nitrate-regulated function of the elements. For example, sequence variants may be generated by site-directed mutation or derived from homologous or orthologous nitrate enhancer elements from other plant species.

The nitrate enhancer elements of the present invention can be linked by a spacer polynucleotide sequence. In some embodiments, the spacer polynucleotide sequence is heterologous sequence. In some embodiments, the spacer sequence is between 5 and 200 nucleotides, or between 5 and 50 nucleotides, or between 40 and 50 nucleotides in length.

The present invention also provides a polynucleotide comprising an expression cassette comprising a nitrate-regulated promoter. As used herein, the term "expression cassette" refers to a polynucleotide comprising a promoter sequence operably linked to other nucleic acid sequences. In some embodiments, the expression cassette comprises an NRP operably linked to a heterologous polynucleotide. The heterologous polynucleotide is useful in expressing heterologous nucleic acids in plants in response to nitrates. In some embodiments, the heterologous polynucleotide is DNA that encodes a polypeptide. In other embodiments, the heterologous polynucleotide codes for an siRNA or antisense RNA that is useful in inhibiting or silencing the expression of desired target genes.

The present invention also provides promoters and expression cassettes that are regulated by nitrites. Nitrites are produced by the reduction of nitrate to nitrite by nitrate reductase. As described in Example 2, an expression cassette comprising the NRPs described above is also strongly induced by nitrite, and the same enhancer elements required for nitrate induction are also required for nitrite induction.

The invention also provides a plant, plant part, seed or plant cell comprising a polynucleotide comprising heterologous nitrate-regulated promoters and expression cassettes described herein. The invention further provides a host cell comprising a polynucleotide comprising the nitrate-regulated promoters and expression cassettes described above. Exemplary host cells include a plant cell, a bacterial cell such as *E. coli*, an animal or mammalian cell, a virus, or any other suitable host cell well known in the art.

B. Promoter Sequences

The present invention provides methods for identifying and isolating promoter sequences that induce or repress genes that are regulated by nitrate. For example, the present invention provides methods for screening for nitrate enhancers in transgenic plants, comprising inserting fragments from nitrate regulated genes into an expression cassette comprising a minimal promoter operably linked to a heterologous polynucleotide, transforming plants with the expression cassette, and assaying for nitrate-induced expression or repression of the heterologous polynucleotide. The production of transgenic plants according to the methods of the present invention is described below. One of skill in the art will recognize that nitrate-regulated promoter and enhancer elements may be isolated from the 5' and 3' untranscribed and/or untranslated regions, as well as the transcribed regions, of nitrate regulated genes. In some embodiments, the heterologous polynucleotide comprises DNA that encodes a reporter gene such as fluorescent yellow protein (FYP) or GUS. In some embodiments, the transgenic plants are assayed for nitrate-induced expression or repression of the reporter gene.

The present invention further discloses the surprising advantage of including a fragment of the NiR promoter in the expression cassette to screen for nitrate enhancer elements from heterologous genes. In one embodiment, the fragment of the NiR promoter that is useful in the methods described herein comprises SEQ ID NO:2 or SEQ ID NO:12. As described in Example 2, the inclusion of a NiR promoter fragment (SEQ ID NO:2 or SEQ ID NO:12) in the NRP increased the activity of the NIA1 enhancer fragment (SEQ ID NO:1 or SEQ ID NO:11) by about 10-fold.

The present invention also discloses methods of identifying and isolating nitrate enhancers using a transient transfection assay. For example, the present invention provides methods for screening for nitrate enhancers in a transient transfection assay comprising inserting fragments from the promoter, the transcribed region, or the 5' and 3' untranscribed regions of nitrate regulated genes into an expression cassette comprising a minimal promoter operably linked to a heterologous polynucleotide, as described above, and transfecting the expression cassette. In some embodiments, the expression cassette further comprises a nucleic acid sequence that augments or increases the activity of nitrate enhancers, such as the NiR promoter fragment (SEQ ID NO:2 or SEQ ID NO:12) described above.

The present invention also provides methods for identifying nitrate regulatory mutants in genetic screens. For example, as described in Example 1, the NRP tripartite promoter can be operably linked to a reporter gene such as fluorescent yellow protein (FYP) or GUS and used to generate transgenic plants that are then mutagenized and screened for failure to show induction of the reporter gene in the presence of nitrate.

C. Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Microinjection techniques are known in the art and well described in the scientific and patent literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983).

Transformed plant cells which are derived by any of the above transformation techniques can be cultured to regenerate a whole plant which possesses the transformed genotype and thus the desired phenotype such as seedlessness. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys*. 38:467-486 (1987).

The nucleic acids of the invention can be used to confer desired traits on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna* and *Zea*.

Vectors are a useful component of the present invention. In some embodiments, the present nitrate-responsive promoters and/or promoter control elements of the invention are delivered to a system such as a cell by way of a vector. For the purposes of this invention, such delivery may range from simply introducing the nitrate-responsive promoter and/or promoter control element by itself randomly into a cell, to integration of a cloning vector containing the nitrate-responsive promoter and/or promoter control element. Thus, a vector is not necessarily limited to a DNA molecule such as a plasmid, cosmid or bacteria phage that has the capability of replicating autonomously in a host cell. All other manner of delivery of the nitrate responsive promoters and promoter control elements of the invention are envisioned. In some embodiments, T-DNA vector is used with the present invention. Many useful vectors are commercially available.

It may also be useful to attach a marker sequence to the present nitrate responsive promoter or promoter control element in order to determine activity of such sequences. Marker sequences typically include genes that provide antibiotic resistance, such as tetracycline resistance, hygromycin resistance or ampicillin resistance, or provide herbicide resistance. Specific selectable marker genes may be used to confer resistance to herbicides such as glyphosate, glufosinate or broxynil (Comai et al., *Nature* 317: 741-744 (1985); Gordon-Kamm et al., *Plant Cell* 2: 603-618 (1990); and Stalker et al., *Science* 242: 419-423 (1988)). Other marker genes exist which provide hormone responsiveness.

Nitrate Induction of Gene Expression

Induction of gene expression by nitrates and nitrites was assayed by measuring the amount of endogenous target gene RNA using qPCR and microarray analysis as described in Example 1, or by using a reporter gene (GUS) as described in Example 2.

EXAMPLES

The following examples are offered to illustrate, but not to limit the claimed invention.

Example 1

Identification of Two Nitrate-Nonresponding Mutants

A nitrate-inducible promoter (NRP) was fused to DNA encoding the yellow fluorescence protein (YFP) and transformed into *Arabidopsis*. Homozygous transgenic plants were generated and tested for nitrate-responsive YFP expression using fluorescence microscopy. Seedlings grown four days with 2.5 mM $NH_4$-succinate (on agarose plates with no nitrate) were treated with 20 mM $KNO_3$ or 20 mM KCl (both with 2.5 mM ammonium succinate) for 16 hr then examined for YFP fluorescence. The nitrate-treated seedlings had much stronger root fluorescence than the chloride-treated controls (FIG. 1A) indicating that YFP expression was induced by nitrate in these plants.

Homozygous transgenic plants were then EMS-mutagenized to produce M2 seedlings, of which approximately 35,000 were screened for low YFP fluorescence after nitrate treatment. Initially 68 seedlings with low fluorescence were identified. Retesting in the next generation recovered 6 seedlings. Two mutants Mut21 (nrg1) and Mut164 were selected for further analysis. An example of the reduced fluorescence phenotype observed in the mutants is shown for Mut21 (FIG. 1C-D).

Identification of Mut164 as an Allele of NLP7.

The Mut164 mutation was mapped to a 55 kb fragment demarcated by the genes At4G23930 and At4g24040. All 15 genes within this region were sequenced from the mutant. This analysis revealed a mutation (C to T) in the second exon of At4g24020 (NLP7) that converted proline at position 223 to a serine. Because NLP7 has been identified as a nitrate regulatory gene (Castaings L et al., *Plant J,* 57: 426-435 (2009)), identification of Mut164 in our screen demonstrated that our strategy for identifying nitrate regulatory mutants was working.

Identification of Mut21 as an Allele of NRT1.1.

Figure 2:
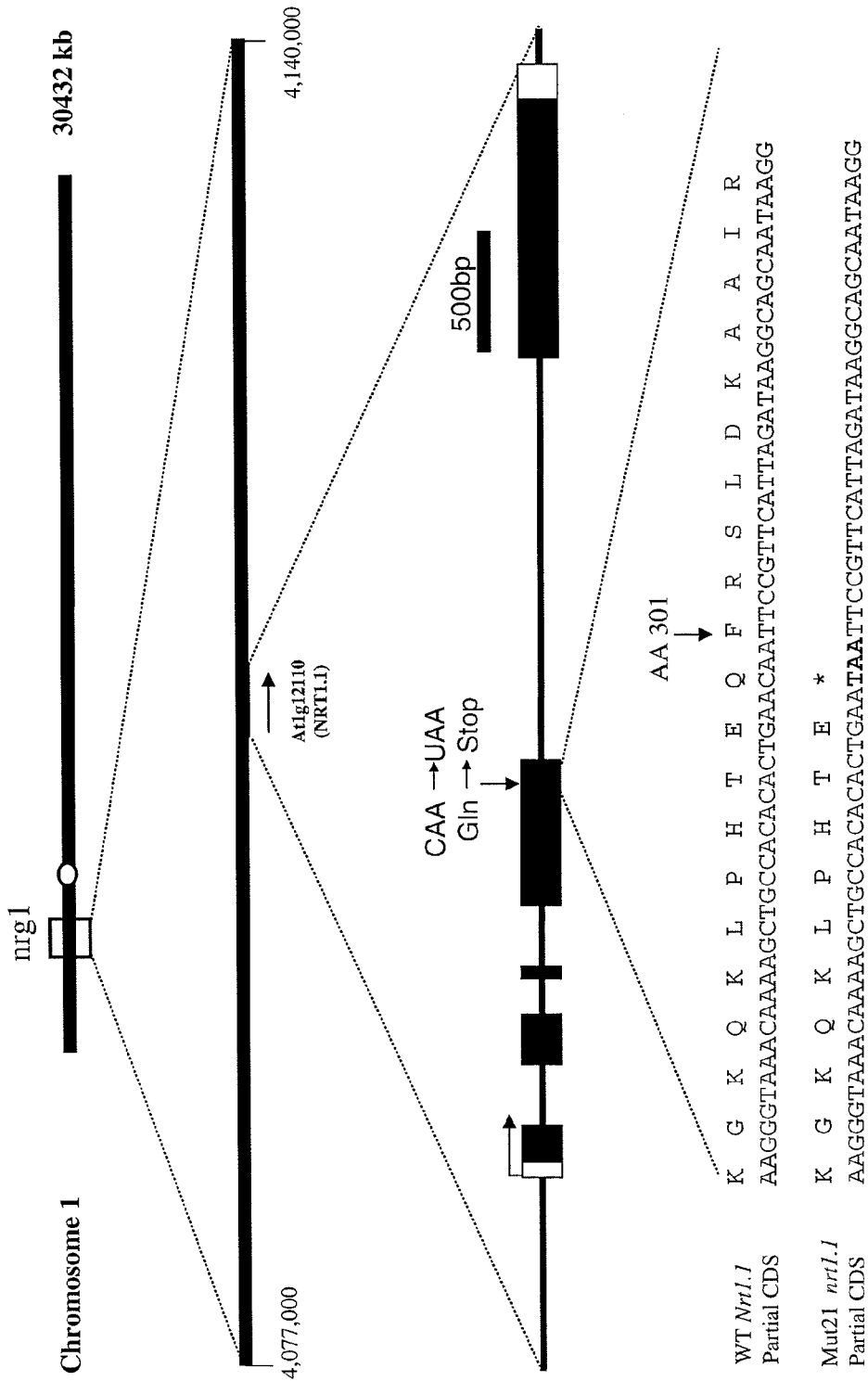
FIG. 2. Mapping of nrg1 (Mut21). Shows schematic diagrams of the *Arabidopsis* chromosome 1 showing where nrg1 mapped. Exons are shown in large black boxes. Amino acid (SEQ ID NOS:17 and 19) and nucleotide (SEQ ID NOS:16 and 18) changes found in Mut21 are also shown.

The nrg1 mutation responsible for the Mut21 phenotype was mapped to chromosome 1 in a region encompassed by BAC clones F12K11 and F20D23 (FIG. 2). This region contained the NRT1.1 (CHL1) gene. RNA transcript analysis by quantitative polymerase chain reaction (qPCR) using oligonucleotide primers to the 3' end of the transcript revealed that there was almost no detectable NRT1.1 transcript in the nrg1 mutant (data not shown). NRT1.1 genomic DNA was amplified and sequenced from nrg1. A mutation was found that converted codon Q301 to a stop codon (FIG. 2). Thus, nrg1 is allelic to NRT1.1.

Nitrate Induction of Gene Expression is Defective in nrg1.

Figure 3:
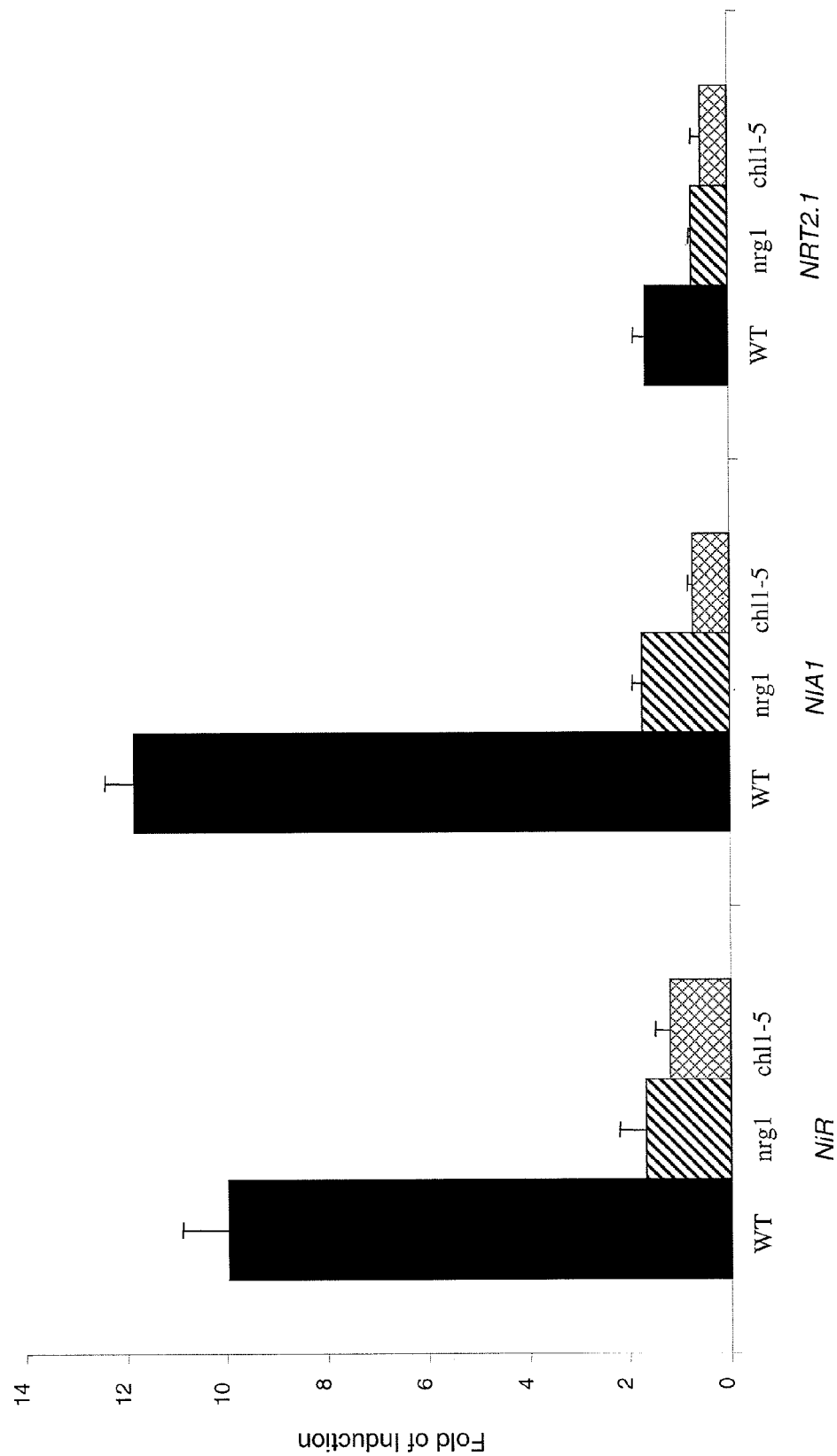
FIG. 3. Nitrate induction of endogenous genes. Wildtype and two nrt1.1 mutant seedlings (nrg1 and chl1-5) were grown on 2.5 mM ammonium succinate for 5 days on agarose plates then treated with either 20 mM $KNO_3$ or 20 mM KCl in the presence of 2.5 mM ammonium succinate for two hours. Root mRNA levels were determined by qPCR. Error bars represent standard deviation of biological replicates (n=3).

Our analysis of nrg1 showed that nitrate induction of the NRP-YFP transgene was greatly diminished. To determine if regulation of endogenous genes was similarly affected, nitrate regulation of several nitrate-inducible genes (NiR, NIA1, NRT2.1) was examined. A well-characterized NRT1.1 mutant (deletion mutant chl1-5, (Tsay Y-F et al., *Cell,* 72: 705-713 (1993); Munos S et al., *Plant Cell,* 16: 2433-2447 (2004))) was included in these experiments to verify that the Mut21 phenotype was due to the mutation in NRT1.1. Plants were grown for 5 days on agarose plates with 2.5 mM $NH_4$-succinate as the sole nitrogen source then treated with 20 mM $KNO_3$ or 20 mM KCl in the presence of 2.5 mM ammonium succinate for two hours. Root mRNA was prepared then analyzed by qPCR. Data in FIG. 3 show that nitrate induction of NiR, NIA1 and NRT2.1 in both nrg1 and chl1-5 was significantly reduced (by greater than 80%) compared to WT. Note that mM ammonium was present during these treatments, which explains the low level of nitrate induction of NRT2.1.

Nitrate Induction of Gene Expression is Restored by N Deprivation in nrg1.

Figure 4:
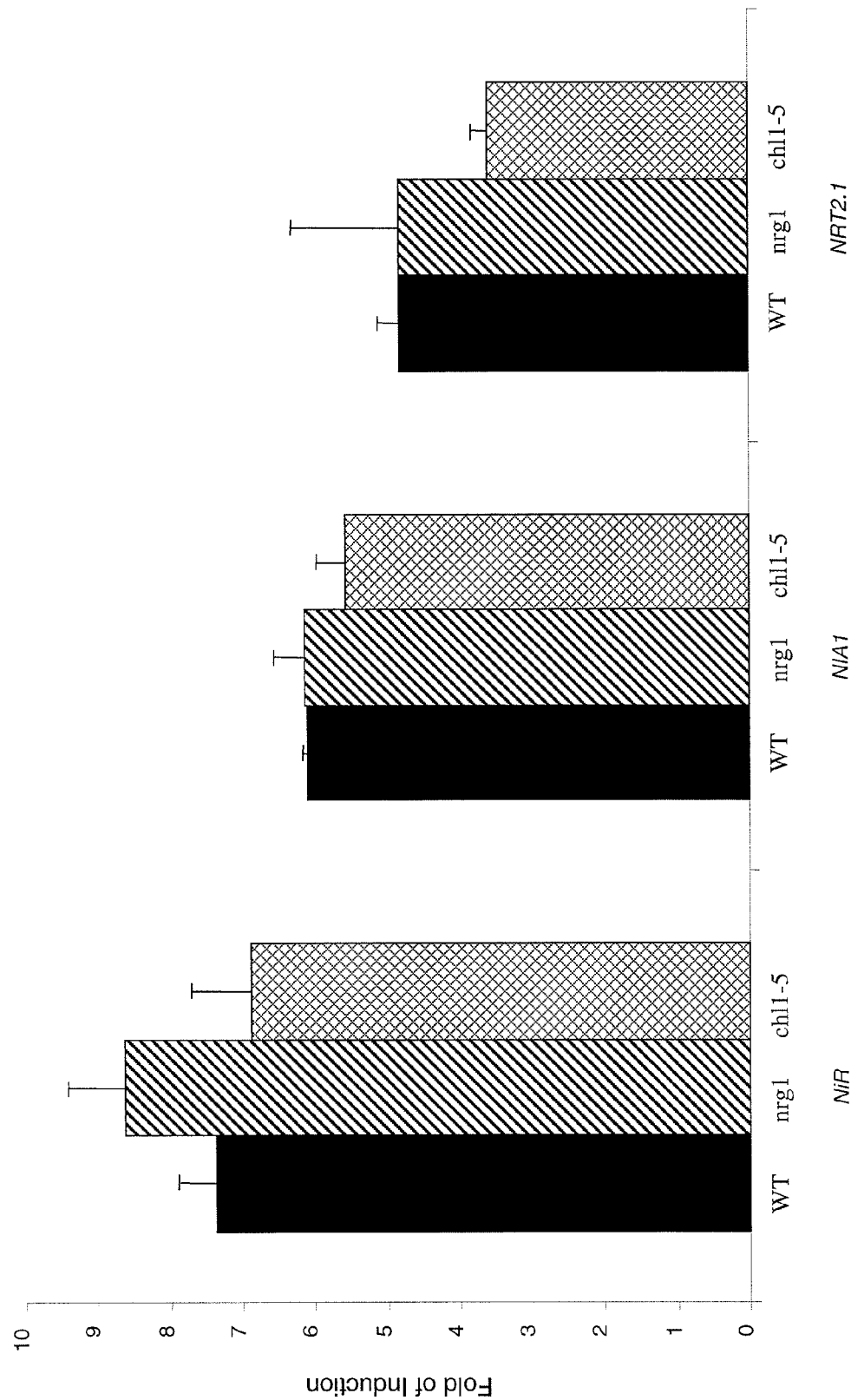
FIG. 4. Nitrate induction of endogenous genes after 24 hr N-deprivation. Plants were grown and treated as described in legend to FIG. 3 except at day 4, plants were transferred to N-free medium for 24 hrs then treated with 20 mM nitrate or chloride for 2 hr with no added ammonium succinate. Root mRNA levels were determined by qPCR. Error bars represent standard deviation (n=3).

The virtual loss of nitrate-induced gene expression by nrt1.1 mutations was a surprise. We have tested for such phenotypes in the past and found little difference between WT and nrt1.1 mutants (unpublished data). Recently, Hu et al., reported a 1.7-2.2 decrease in nitrate induction of NiR, NIA1 and NRT2.1 in chl1-5 mutants compared with WT (Hu H C et al., *Plant J,* 57: 264-278 (2009)), which is much less than what we observed (see FIG. 3). Upon comparison of experimental protocols, we noticed that our previous conditions included a N starvation pretreatment to enhance the nitrate response, which was not done in our current experiments with Mut21. To determine if the Mut21 phenotype is affected by N deprivation, the previous nitrate induction experiment, in which plants were exposed continuously to N in the form of ammonium (FIG. 3), was repeated except that seedlings were first N-deprived for 24 h before nitrate treatment. The results show almost no loss of nitrate induction in mutant plants (FIG. 4) indicating that N starvation for 24 hr had restored nitrate induction in Mut21 and thus rendered the nitrate response NRT1.1-independent.

To determine how long it takes to lose NRT1.1-dependent induction upon N starvation, a time course experiment was performed. Plants were grown hydroponically on 2.5 mM ammonium succinate for seven days then N-starved by transfer to the same media with no ammonium succinate. Plants were then treated with 1 mM KCl or $KNO_3$ for 30 min. Root were harvested, mRNA prepared and analyzed by qPCR. The data show that for all three genes tested (NiR, NIA1 and NRT2.1), nitrate induction began to recover in the mutant after 1-2 hr of N-starvation. After 24 hr, nitrate induction in the mutant was almost as high as for wildtype plants.

The effect of N starvation on NRT1.1 expression was measured to determine if the loss of the Mut21 phenotype could be accounted for by a loss of NRT1.1 mRNA. Over the first 8 hours of N starvation, the level of NRT1.1 mRNA increased about 1.6-fold. However, after 24 hr, the level dropped 4-fold. These results indicate that the loss of NRT1.1-dependent regulation during the first 8 hours of N starvation is not due to the loss of NRT1.1 expression (i.e. mRNA) and may be due to a post-transcriptional modification. At 24 hr, the drop in NRT1.1 mRNA was sufficiently large that it should contribute to the loss of the Mut21 phenotype.

The experiments described above cannot determine where it is the N deprivation in general or the loss of ammonium in particular that is responsible for the loss of the Mut21 phenotype. Including 5 mM ammonium during the 2 hr nitrate induction treatment of N-starved seedlings did not restore the Mut21 phenotype (data not shown). Further experiments are needed to resolve this issue.

Loss of Nitrate Induction in nrg1 is not Accounted for by Impaired Nitrate Uptake.

Figure 5:
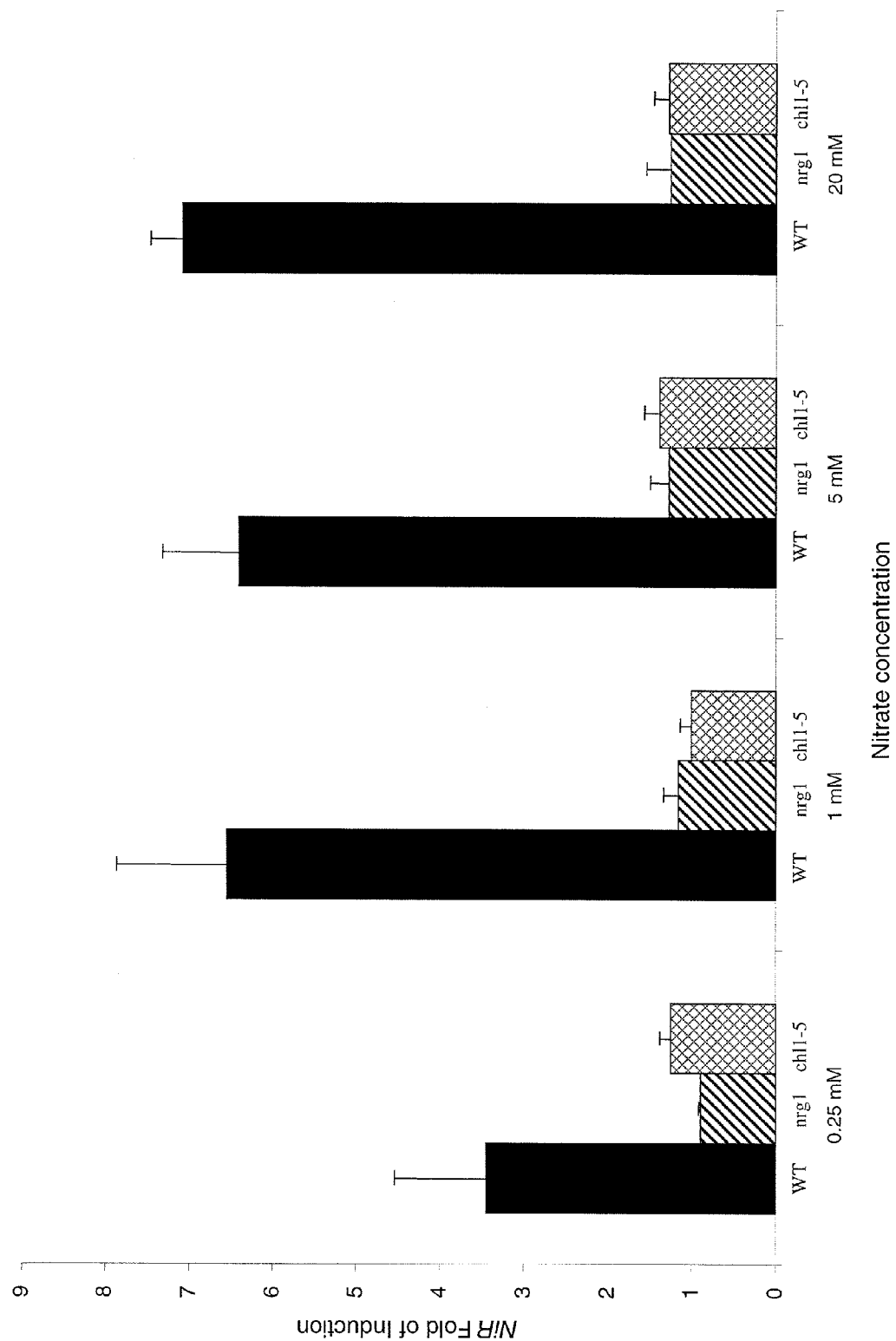
FIG. 5. Titration of the nitrate induction response. Seedlings were grown 5 days on agarose plates with 2.5 mM ammonium succinate (same as FIG. 3) then treated with various concentrations of $KNO_3$ or KCl for 2 hours in the presence of 2.5 mM ammonium succinate before roots were collected for RNA preparation. NiR mRNA levels were determined by qPCR. Error bars represent standard deviation (n=3).
Figure 6:
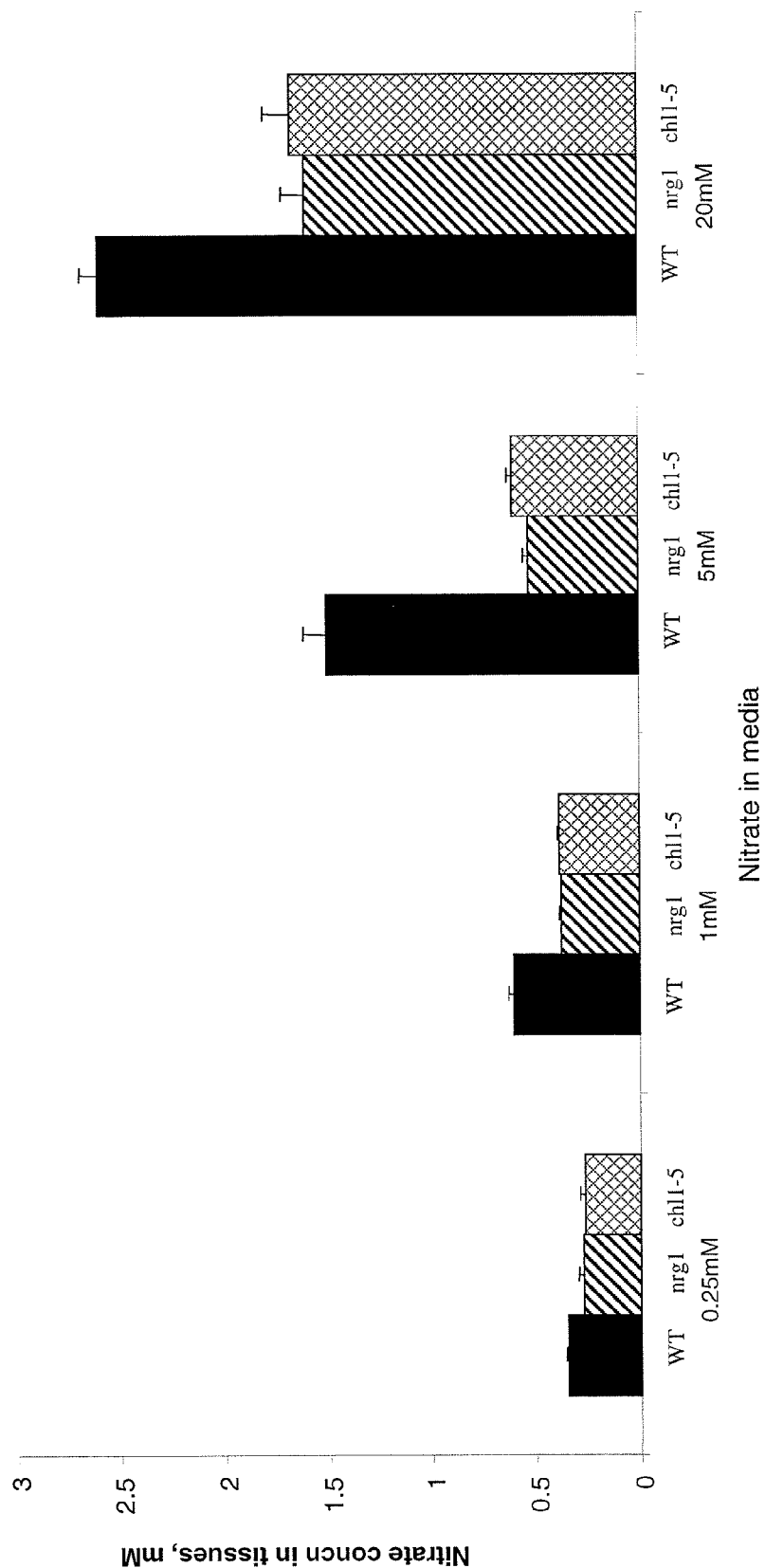
FIG. 6. Nitrate accumulation. Seedlings grown 5 days with 2.5 mM ammonium succinate were treated with various concentrations of $KNO_3$ (same as for FIG. 5) in the presence of 2.5 mM ammonium succinate for 2 h. Whole seedlings were then collected for nitrate assays as described in Materials and Methods. Error bars represent standard deviation (n=3).

Since NRT1.1 encodes a nitrate transporter, it is possible that the loss of nitrate induction in the nrt1.1 mutants is due to reduced nitrate uptake. To test this idea, nitrate induction of NiR in WT and the two nrt1.1 mutants were assayed at various concentrations of nitrate (0.25-20 mM) in the presence of ammonium (FIG. 5). Nitrate induction was virtually abolished in both mutants at all nitrate concentrations tested under these conditions. Next, nitrate accumulation in whole seedlings was also measured after the same 2 hr treatments (FIG. 6) under the same conditions. Nitrate accumulation was lower in the mutants than the WT at all the concentrations of nitrate tested; however, the amount of accumulation was still substantial enough in the mutants (36-77% of WT) to support nitrate induction. For example, nitrate accumulation at 20 mM nitrate in the mutants is as much or more than in WT plants treated with 0.25 mM to 5 mM nitrate, yet nitrate induction is vanishing small in the mutants at 20 mM nitrate (FIG. 6). In fact, the amount of nitrate entering the plants under all concentrations tested is more than sufficient for induction, as uptake from solutions with only 2-5 µM nitrate is needed for strong induction (Wang R et al., *Plant Physiol*, 145: 1735-1745 (2007)). Thus, reduction in nitrate uptake cannot explain the loss of nitrate induction in the mutants.

Microarray Analysis of Nitrate-Response in nrt1.1 Mutants.

Several transcriptome analyses have been reported for nrt1.1 mutants. In addition to the SAGE experiments for plants grown on ammonium nitrate (Munos S et al., *Plant Cell*, 16: 2433-2447 (2004)), a microarray analysis using ATH1 chips of nitrate-treated (30 min at 25 mM) roots found that 42 genes had absolute transcript levels that were lower in the chl1-5 mutant by 1.7-fold or more (or 17 genes reduced by 2-fold or more) compared with WT (Hu H C et al., *Plant J*, 57: 264-278 (2009)). We performed microarray analyses in a different way: using both control and nitrate-treated WT and nrg1 plants that had been grown without N-starvation (i.e. with continuous ammonium supply) to determine the effect of nrg1 on nitrate induction ratios under these conditions. Seven-day old plants grown under hydroponic conditions with ammonium were treated with 1 mM KCl or $KNO_3$ in the presence of ammonium for 30 min. Root mRNA was isolated and analyzed using ATH1 chips.

The microarray data showed that 111 genes had lower induction ratios of 2-fold or more in nrg1 plants and only 3 genes had higher induction ratios of 2-fold or more in nrg1 plants. Many known nitrate-inducible genes including NiR (induction ratio reduced 5.1-fold in mutant), NIA1 (reduced 4.0-fold), UPM1 (reduced 3.8-fold), NIA2 (reduced 2.5-fold) and NRT2.4 (reduced 2.0-fold) showed reduced nitrate induction ratios in the mutant. CIPK1 and CIPK3 were also on this list consistent with the findings of Hu et al. (Hu H C et al., Plant J, 57: 264-278 (2009)). Biomaps analysis using the MIPS database (see the world wide web at virtualplant.org) revealed that genes most affected by the nrg1 mutation were over represented in Gene Ontology groups: energy, photosynthesis, pentose-phosphate pathway, detoxification and light absorption.

Materials and Methods

Plant Materials and Growth Conditions

Mutagenesis: Homozygous backcrossed transgenic seeds containing the NRP-YFP construct (1.2 g in 20 ml of water) were treated with EMS (methanesulfonic acid ethyl ester) at 15 mM for 16 hr with agitation (30 rpm). M2 seeds were produced and pooled into families for screening. NRP contained promoter fragments from the NIA1 and NiR promoters fused to the 35S minimal promoter (see Genbank Accession #GQ374175) (SEQ ID NO:15).

Mutant screen: M2 seedlings were screened on vertical 100×100 mm square plates containing 25 ml of 0.6% agarose media. Surface sterilized seeds were aligned horizontally on the plate surface at a density of about 100 seeds per row. Three rows of seeds were placed on each plate. The initial medium (described in (Wang R et al., *Plant Physiol*, 136: 2512-2522 (2004))) was nitrate-free with 2.5 mM ammonium succinate as the nitrogen source. After incubation at 4° C. for two days, seedlings were grown at 25° C. with 24 hr light. Four-day old seedlings were then flooded with 12.5 ml of medium containing 20 mM $KNO_3$ and 2.5 mM ammonium succinate for 16 hr. Seedling were screened under a fluorescence microscope (Nikon Eclipse TE2000-U) and rescued. Putative mutants were selfed then rescreened. Confirmed mutants were backcrossed to the transgenic WT and made homozygous before analysis.

Growth and treatment conditions: For qPCR analyses and nitrate accumulation assays, seedlings were grown on vertical agarose plates as described above for 5 days with 2.5 mM ammonium succinate as the sole nitrogen source in plant growth medium (Wang R et al., *Plant Physiol*, 136: 2512-2522 (2004)). The seedlings were then flooded with 12.5 ml of plant growth medium (with 2.5 mM ammonium succinate) plus $KNO_3$ at various concentrations for 2 hr with agitation (60 rpm) under light. Roots were then collected for total RNA preparation (as described (Wang R et al., *Plant Physiol*, 132: 556-567 (2003))). Control samples were prepared at the same time with the same concentration of KCl in place of $KNO_3$.

For nitrate treatments without ammonia, seedlings were grown on plant growth medium with 2.5 mM ammonium succinate for 4 days then transferred to fresh agarose plates without nitrogen for 24 hr followed by flooding with nitrate containing plant growth media as described above except that there was no ammonium succinate in the liquid medium.

For the microarray analysis, plants were grown in aseptic hydroponics as described (Wang R et al., *Plant Physiol*, 145: 1735-1745 (2007)) for 7 days with modifications as follows: Seedlings were transferred to 100 ml of fresh medium with 2.5 mM ammonium succinate after 6 days of growth and continued incubation for 24 hr. Nitrate and control chloride treatments were initiated by adding $KNO_3$ or KCl to the growth media to yield 1 mM concentration then incubated for 30 min before harvesting roots.

Gene Expression and Nitrate Analysis qPCR analysis: RNA samples were prepared from roots as described (Wang R et al., *Plant Physiol*, 145: 1735-1745 (2007)). Real-time quantitative PCR was performed as described (Wang R et al., *Plant Physiol*, 136: 2512-2522 (2004)). Relative expression levels of NRT1.1 were compared with the internal reference gene, UBQ-associated protein gene (At5g12120).

Microarray analysis: Roots were collected for total RNA preparation as described (Wang R et al., *Plant Physiol*, 145: 1735-1745 (2007)). Experiments were done in duplicate then averaged to generate induction ratios using the Affymetrix software as described (Wang R et al., *Plant Physiol*, 132: 556-567 (2003)). In all cases, data were filtered to require that signal levels were detectable in both replicates for at least one of the treatments (indicated as "P" by the Affymetrix software) and had an absolute value of 100 or more.

Nitrate accumulation: Nitrate in seedlings of WT and mutants were measured using the hydrazine-sulfate method as described (Wang R et al., *Plant Physiol*, 136: 2512-2522 (2004)).

Positional cloning of nrg1 was performed on individual F2 recombinants using simple sequence length polymorphisms as described (Lukowitz W et al., *Plant Physiol*, 123: 795-805 (2000)).

This example demonstrates that a nrt1.1 mutant can be captured in a genetic screen for nitrate regulatory mutants and that nrt1.1 mutants are impaired in nitrate regulation of gene expression over a wide variation of nitrate concentrations.

Example 2

Identification of a Nitrate Enhancer Fragment in the NIA1 Promoter

Figure 7:
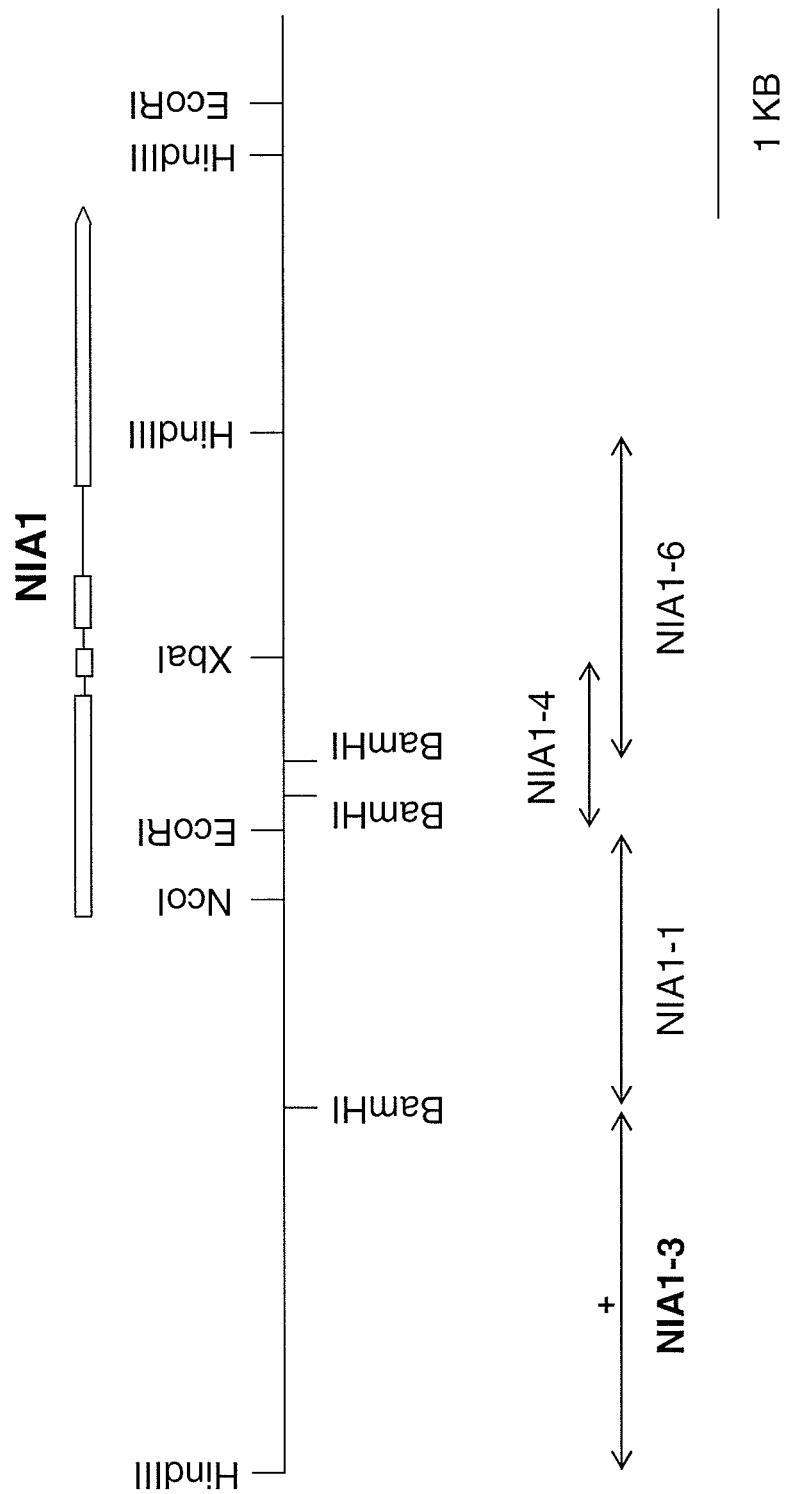
FIG. 7. Nitrate enhancer screen for NIA1 gene. Fragments NIA1-1 to NIA1-6 were tested in transgenic plants for nitrate enhancer function. Only the NIA1-3 fragment (shown in bold and with "+") showed nitrate-inducible GUS activity. The diagram above the restriction map shows the transcribed region of NIA1 with open boxes showing exons.

Fragments from promoter and transcribed regions of the nitrate reductase gene NIA1 (At1g77760) were cloned into a vector containing a 35S minimal promoter (SEQ ID NO:3) fused to GUS. Constructs were transformed into *Arabidopsis* plants using *Agrobacterium* and tested for nitrate-inducible GUS expression. Transgenic plants were grown for ten days on ammonium succinate as the sole N source then treated with 10 mM $KNO_3$ for 24 hrs before assaying for GUS activity using histochemical staining. Out of four NIA1 fragments tested, only one (the 1.8 kb NIA1-3 fragment, which is located in the distal promoter region 5' to the start of transcription) showed nitrate enhancer activity (FIG. 7). The other fragments showed baseline activity similar to that of the 35S minimal promoter alone.

Figure 8:
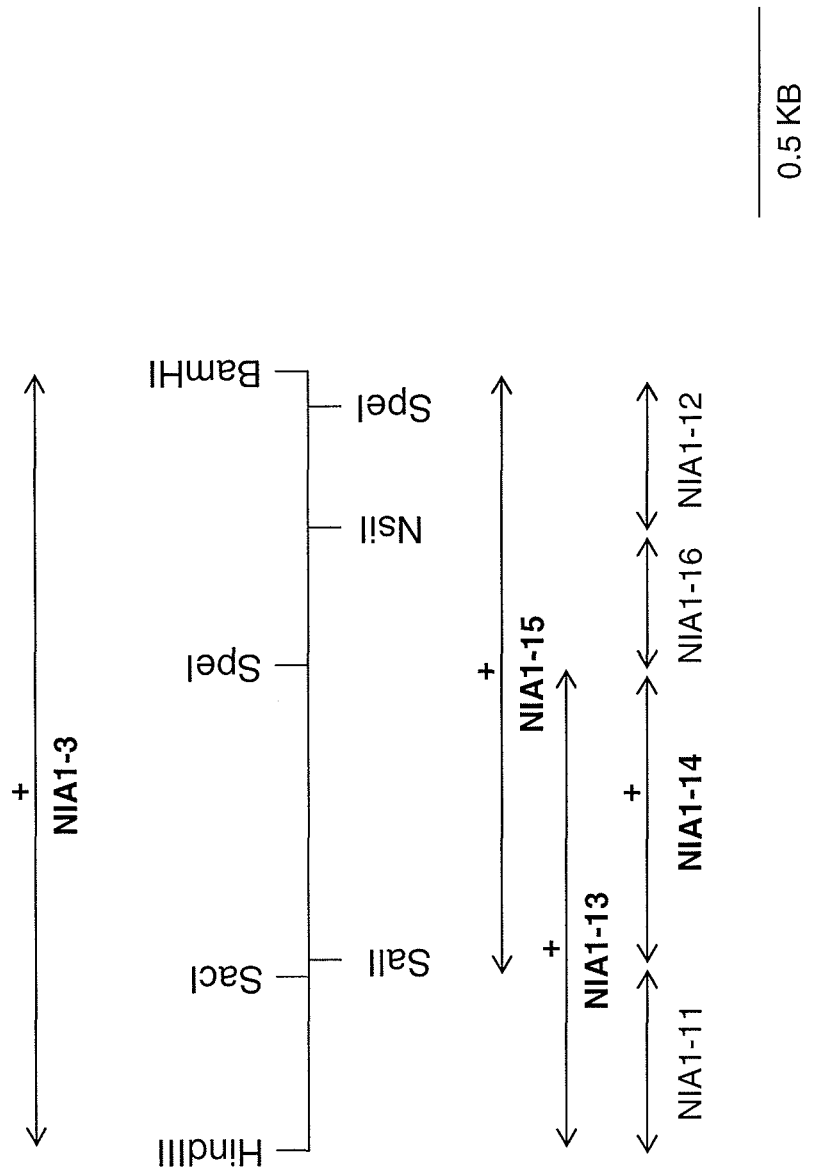
FIG. 8. Enhancer analysis of sub-fragments of NIA1-3. Fragments in bold and with "+" showed nitrate-inducible GUS activity in transgenic *Arabidopsis*. Other fragments did not show such activity.
Figure 9:
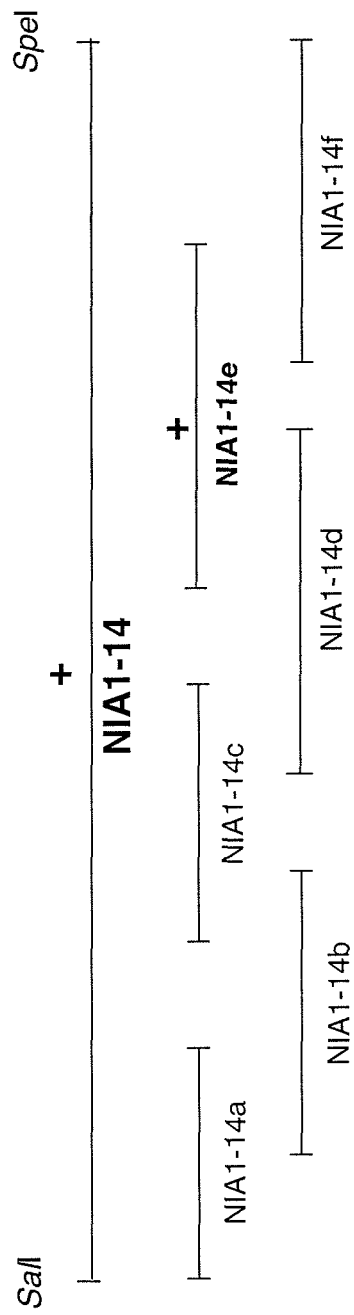
FIG. 9. Enhancer analysis of NIA1-14. Fragments in bold and with "+" showed nitrate-inducible GUS activity in transgenic *Arabidopsis*. Other fragments did not show such activity.

The 1.8 kb NIA1-3 DNA was subdivided into smaller fragments (FIG. 8) and tested again with the 35S minimal promoter in transgenic *Arabidopsis* plants. Enhancer function was localized to a 640 bp fragment (NIA1-14). NIA1-14 was subdivided further into 150-200 bp overlapping fragments and then tested; only one fragment (NIA1-14e, 180 bp) (SEQ ID NO:1; SEQ ID NO:11) showed nitrate enhancer activity (FIG. 9).

Construction and Analysis of a Strong Nitrate-Inducible Promoter: NRP.

Figure 10:
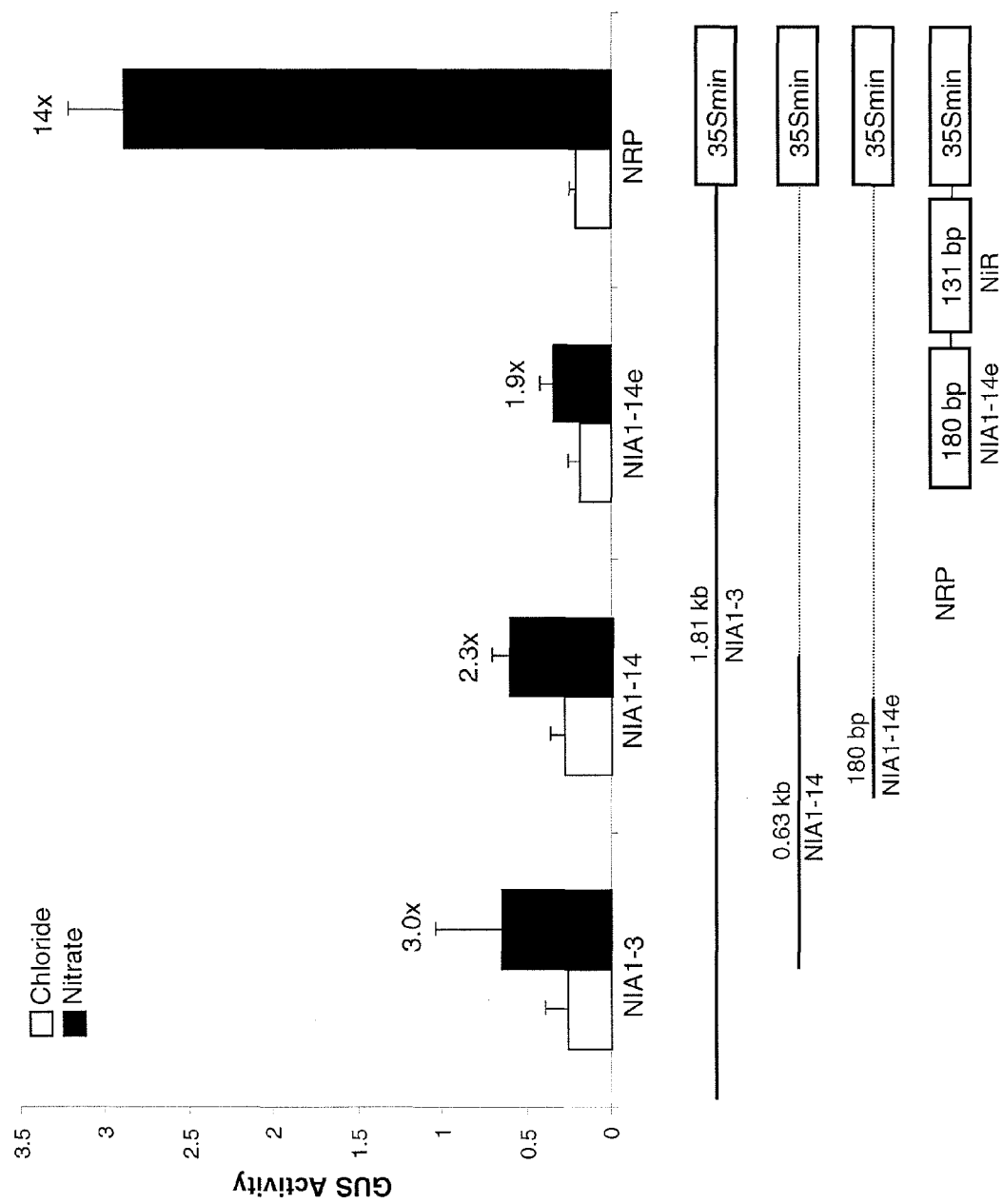
FIG. 10. Nitrate enhancer analysis of NIA1 promoter fragments in *Arabidopsis* transgenic lines. Transgenic seedlings grown on agarose plates with ammonium and no nitrate were transferred to plates containing 10 mM nitrate or 10 mM chloride for 24 h then assayed for promoter (GUS) activity as described in Materials and Methods. The averages of three independent transgenic lines are shown (error bars show standard error, GUS activity shown as nmol/(mg protein-hr)). Each GUS assay was performed in triplicate for each transgenic line. The fold of nitrate induction is indicated above each bar. The diagrams under the histogram show the promoter constructs used for these experiments.

To quantify the nitrate induction levels for each of the positive clones described above, transgenic plants were analyzed using the quantitative GUS assay as described in Materials and Methods. Constructs containing the largest fragment, NIA1-3 (1.8 kb), showed 3.0-fold induction (averaged for three independent transgenic lines) while the NIA1-14 (630 bp) and NIA1-14e (180 bp) (SEQ ID NO:11) fragments showed 2.3-fold and 1.9-fold induction, respectively (FIG. 10). These results showed that reducing the size of the enhancer DNA reduced the level of induction. Efforts to subdivide NIA144e into smaller fragments, which included testing overlapping 30 bp fragments in triplicate, were unsuccessful in further localizing the enhancer activity.

In order to continue with our search for specific enhancer elements, a search was made for DNA sequences that could augment the enhancer activity of the 180 bp NIA1 fragment (SEQ ID NO:11). We tested several fragments near the start of transcription of the *Arabidopsis* NiR gene because several reports showed that NiR promoter constructs were nitrate inducible in transgenic plants (Wilkinson J Q, *Molecular and genetic characterization of the nitrate reductase structural genes (NIA1 and NIA2) of Arabidopsis thaliana*, University of California at San Diego, La Jolla, Calif. (1992); Rastogi R et al., *Plant J.*, 4: 317-326 (1993); Neininger A et al., *Planta*, 194: 186-192 (1994); Sander L et al., *Plant Mol Biol.*, 27: 165-177 (1995); Rastogi R et al., *Plant. Mol. Biol.*, 34: 465-476 (1997); Dorbe M-F et al., *Plant Sci.*, 139: 71-82 (1998)). A 475 bp NiR fragment showing nitrate induction in transgenic *Arabidopsis* plants was divided into two fragments (upstream 260 bp and downstream 215 bp fragments relative to the start of transcription) and inserted between the 180 bp NIA fragment (SEQ ID NO:11) and the 35S minimal promoter (SEQ ID NO:3). The 260 bp NiR fragment strongly boosted the nitrate enhancer activity of the 180 bp NIA1 fragment while the 215 bp fragment showed no effect. The 260 bp NiR fragment was not serving simply as a spacer as 260 bp of *E. coli* DNA showed little effect. The 260 bp and 215 bp NiR fragments alone (with just the 35 minimal promoter) had little to no activity. The 260 bp NiR fragment was subdivided into three overlapping fragments and tested with the 180 bp NIA1 fragment. The most 3' fragment (131 bp R) (SEQ ID NO:2; SEQ ID NO:12) showed the strongest effect while the other two (130 bp L and M) showed little to no activity. We subsequently used the tripartite promoter, containing the 180 bp NIA1-14e (SEQ ID NO:11), 131 bp R NiR (SEQ ID NO:12) and 35S (SEQ ID NO:3) minimal fragments and called "NRP" for nitrate-regulated promoter (SEQ ID NO:15), for subsequent experiments.

Figure 11:
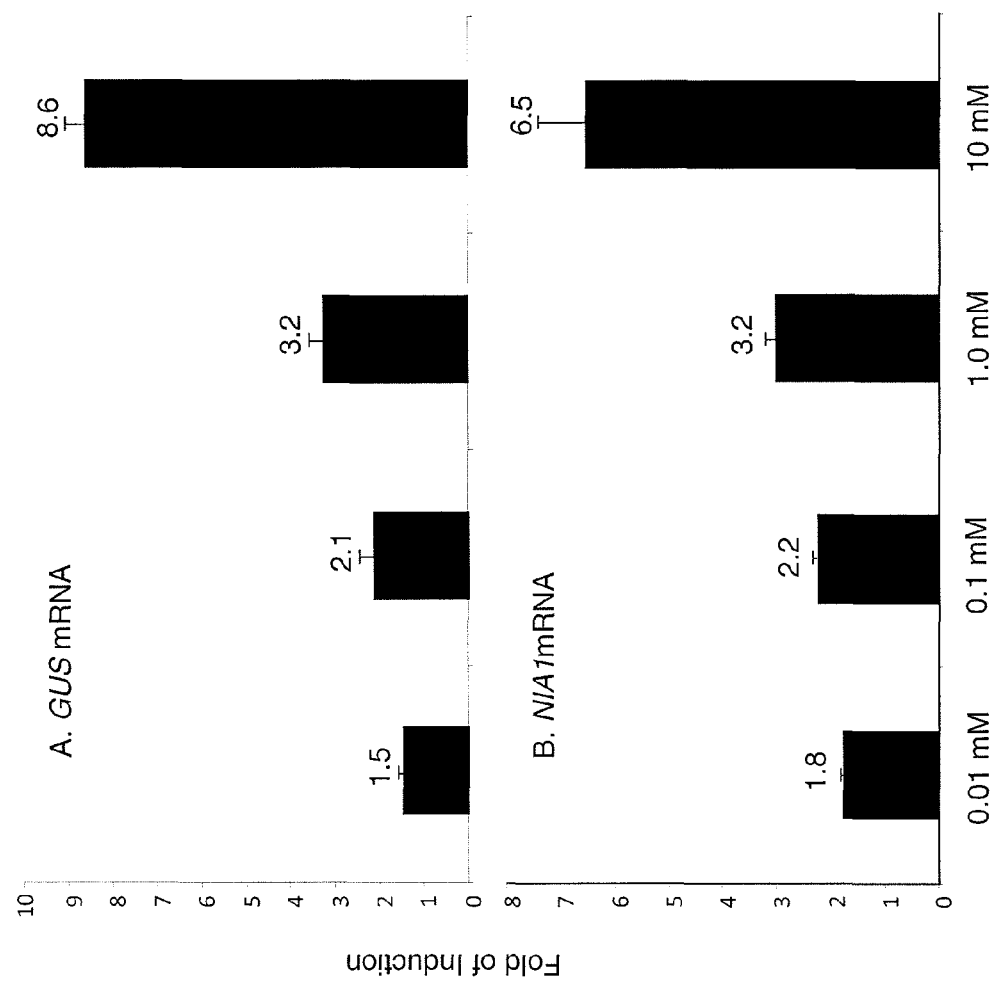
FIG. 11. Nitrate induction of NRP-GUS mRNA in transgenic lines. NRP-GUS transgenic plants (line R56-3) were grown on agarose plates with nitrate-free growth media containing 2.5 mM ammonium succinate for 9 d under continuous light. The plates were then flooded with 15 ml of fresh medium plus $KNO_3$ or KCl for 20 min at concentrations as indicated. Roots were collected for total RNA preparation at end of treatments. NIA1 and GUS mRNA levels were assayed by real-time quantitative PCR (Wang R et al., *Plant Physiol.*, 145: 1735-1745 (2007)) with clathrin (At4g24550) as the reference gene. Experiments were in triplicate, and error bars show standard error.

Using the quantitative GUS assay, we found that the NRP-GUS construct showed 14-fold induction, which was much higher than the 1.9-fold induction found for the 180 bp NIA1 fragment (SEQ ID NO:11) alone (FIG. 10). A nitrate titration was performed with the NRP-GUS construct by analyzing GUS mRNA levels in roots after treating transgenic plants with nitrate at various concentrations for 20 min (FIG. 11). Nitrate inductions of 2-fold or more were observed at 100 µM nitrate concentrations or greater, and the dose-response was similar to the nitrate induction observed for the endogenous NIA1 gene.

Figure 12:
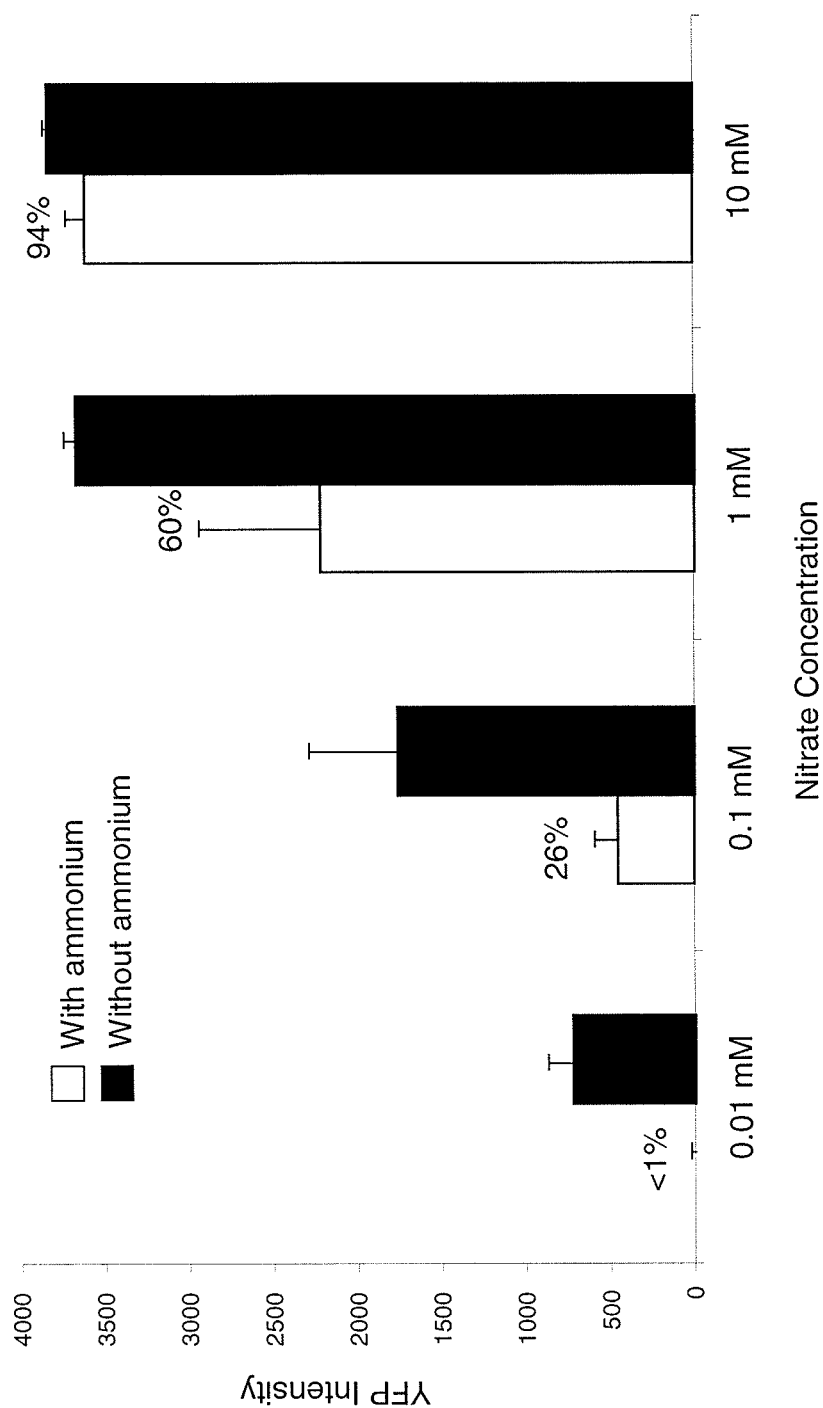
FIG. 12. Ammonium repression of NRP promoter. NRP-YFP transgenic plants were grown on vertical agarose plates for 4 d with 2.5 mM ammonium succinate as the sole nitrogen source. The seedlings were then transferred to fresh plates with media containing $KNO_3$ at the indicated concentrations with or without 2.5 mM ammonium succinate. Seedlings transferred to plates without nitrate in the presence or absence of 2.5 mM ammonium succinate were used as controls. Seedlings were incubated under continuous light for 16 h then YFP fluorescence was determined by fluorescence microscopy with ImageJ software (NCBI). Each data point represent an average of 6 readings with standard error as indicated. The numbers above the open bars show the percent of fluorescence intensity in nitrate-treated plants treated with ammonium compared with nitrate-treated plants without ammonium.

Another feature of many nitrate-induced genes is feedback repression (Girin T et al., *Plant Cell Environ.*, 30: 1366-1380 (2007)). The NRP construct was tested for ammonium repression by treating transgenic plants with nitrate in the presence or absence of ammonium. Transgenic *Arabidopsis* plants containing an NRP-YFP construct were grown on ammonium as the sole N source then treated with nitrate for 16 hr at various concentrations of nitrate in the presence or absence of 5 mM ammonium (FIG. 12). At low nitrate concentrations, the presence of ammonium strongly reduced the amount of NRP-YFP expression (99% inhibition at 0.01 mM nitrate and 74% inhibition at 0.1 mM nitrate). At higher nitrate concentrations, ammonium had much less effect (only 40% inhibition at 1 mM nitrate and 6% inhibition at 10 mM nitrate). These results show that the enhancer fragments in NRP retain sensitivity to ammonium repression, which is most apparent at low nitrate levels.

Development of a Transient Expression System to Assay Nitrate Enhancers.

To accelerate the identification of enhancer elements, a transient expression system was developed using Agroinfiltration of *Nicotiana benthamiana*. This system has been used to study protein expression (Kopertekh L, Schiemann J, *Transgenic Research*, 14: 793-798 (2005); Joensuu J J et al., *Plant Physiol.*, 152: 622-633 (2010)), gene silencing (Waterhouse P M, Helliwell Calif., *Nature Reviews Genetics*, 4: 29-38 (2003); de Felippes F F, Weigel D, *Methods Mol Biol*, 592: 255-264 (2010)), and protein-protein interactions (Ohad N, *Plant Physiology*, 145: 1090-1099 (2007)). It has also been used for promoter analysis (Yang Y N et al., *Plant Journal*, 22: 543-551 (2000)). We adapted it for our nitrate-regulated promoters by growing plants on nitrate-free media with ammonium as the sole nitrogen source before Agroinfiltration then irrigating plants with 10 mM $KNO_3$ to induce gene expression. $KNO_3$ was replaced with KCl for control plants. Leaves were assayed for promoter (GUS) activity 3-4 days after infiltration.

Figure 13:
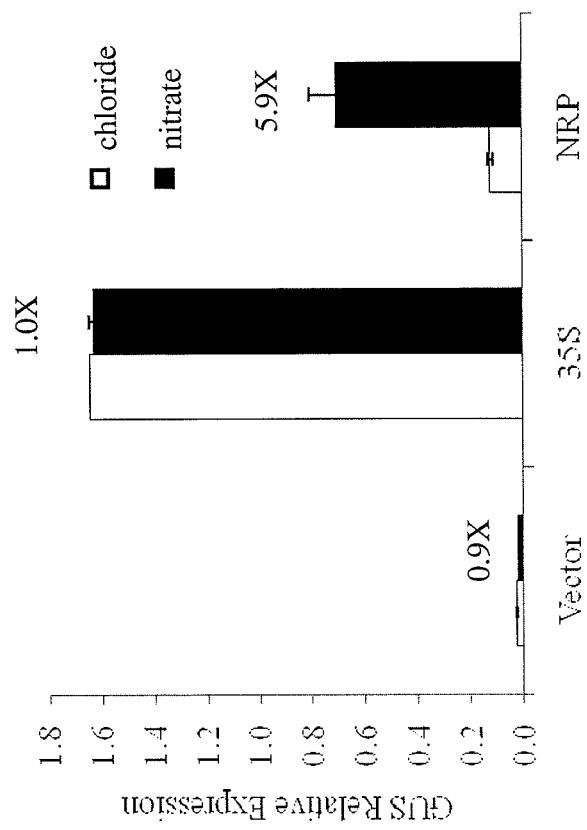
FIG. 13. Testing the *N. benthamiana* transient expression system. Leaves of *Nicotiana* were infiltrated with *Agrobacteria* containing the indicated promoter constructs fused to GUS then assayed 3-4 days later for GUS activity as described in Materials and Methods. Plants were irrigated with either 10 mM KCl or 10 mM $KNO_3$ 30 min before infiltration and 24 hr before harvest. Experiments were done in triplicate with error bars showing standard error. Numbers above the bars show fold induction. Labels are as follows: Vector: 35S minimal promoter; 35S: 35S full length promoter; NRP: tripartite promoter containing the NIA1 180 bp, MR 131 bp and 35S minimal promoter fragments.
Figure 14:
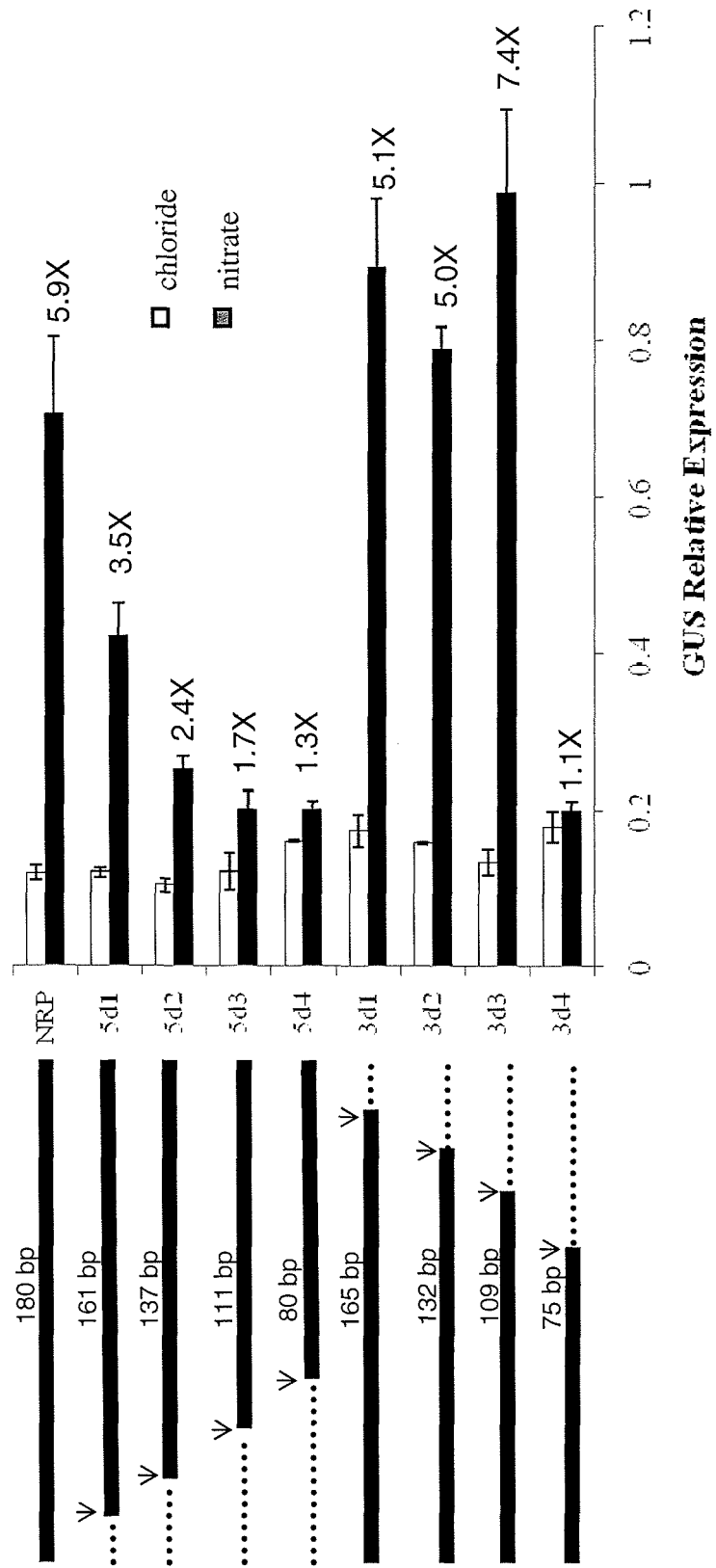
FIG. 14. Deletion analysis of the NIA1 180 bp enhancer fragment. Deletions of the NIA1-14e fragment are shown to the left of the histogram. Deletion endpoints are shown with arrowheads, and remaining nucleotides are shown with solid black line. The histogram shows GUS activities after nitrate and chloride treatments with fold inductions showed to the right of each bar. Experiments were done in triplicate with error bars showing standard error.

When *Nicotiana* leaves were infiltrated with *Agrobacteria* containing the vector alone (just the 35S minimal promoter fused to GUS), very low levels of GUS activity were observed in nitrate and chloride-treated leaves (FIG. 13, Vector). Infiltration with a full-length 35S promoter fused to GUS showed very high, unregulated activity (FIG. 13, 35S). In contrast, the NRP tripartite promoter, which showed strong nitrate induction in transgenic *Arabidopsis* plants, also showed strong nitrate induction in the transient system (FIG. 13, NRP). Thus, the *Nicotiana* system can be used to assay nitrate-responsive promoters.

Three NEEs Identified in the 180 bp Nitrate Enhancer Fragment.

The search for nitrate enhancer elements in the 180 bp NIA1-14e fragment (SEQ ID NO:11) began with a deletion analysis using the *Nicotiana* transient expression system. NIA1-14e deletion fragments were tested in the context of the tripartite promoter; that is, they replaced the wildtype 180 bp NIA1 fragment in the NRP-GUS construct. A series of 3' deletions of NIA1-14e showed that 71 bp could be deleted with no loss of nitrate induction but that a 105 bp deletion eliminated the response (FIG. 14, 3d1-3d4). At the 5' end, even the first deletion reduced nitrate induction as follows: deletion of 19 bp (FIG. 14, 5d1) reduced induction by 40%; deletion of 43 bp (FIG. 14, 5d2) reduced it by 60%. These results show that the 3' end of NIA1-14e is dispensable and that a 109 bp sub-fragment of NIA1-14e (3d3) (SEQ ID NO:10) is sufficient for full activity.

Figure 15:
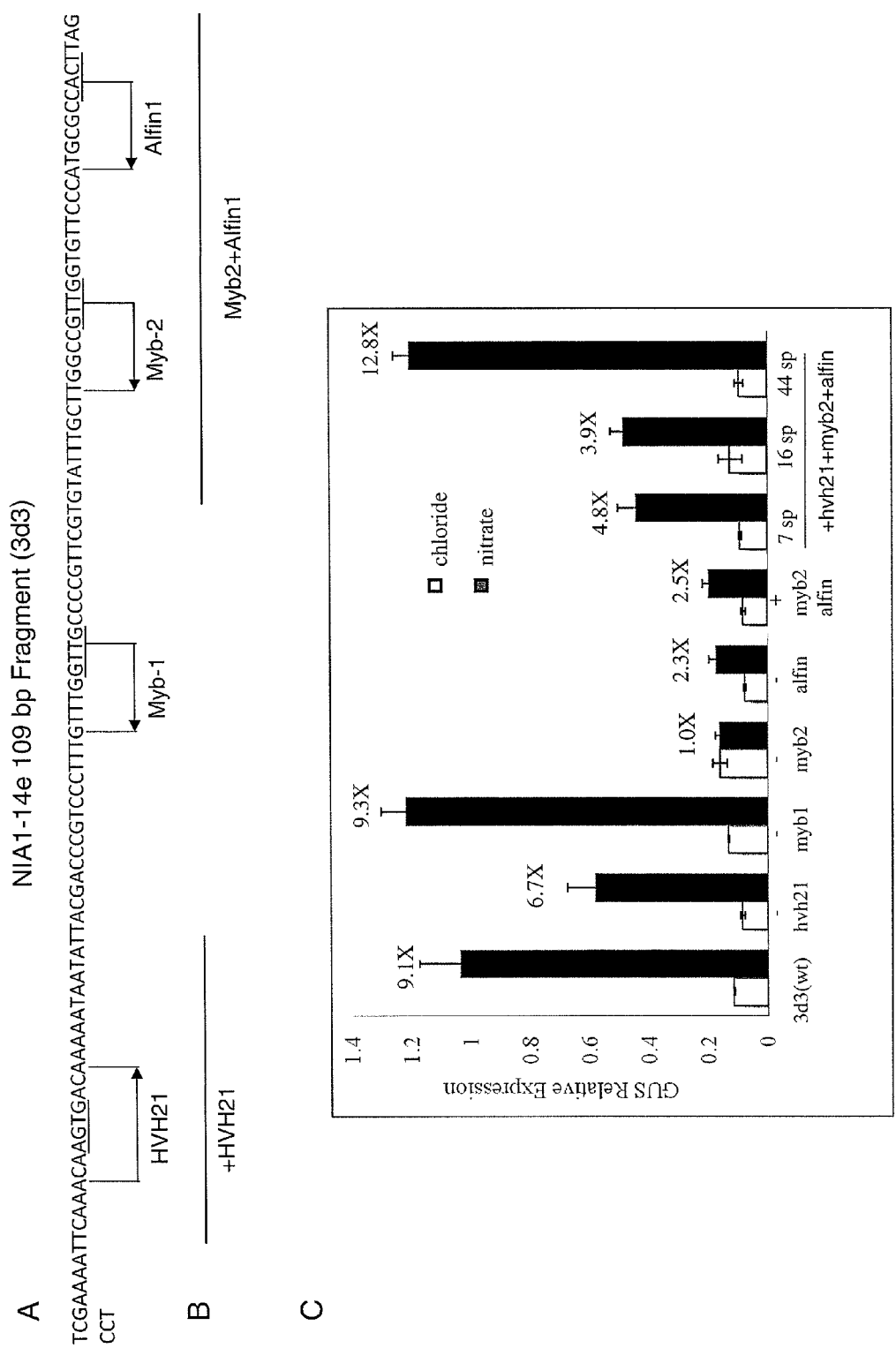
FIG. 15. Identification of enhancer elements in the 109 bp NIA1 enhancer fragment. (A) Sequence of the 109 bp fragment (SEQ ID NO:10) showing sites of transcription factor binding sites as predicated by AthaMap. The 4 bp deletions that were tested are underlined. (B) Location of the HVH21 and Myb-2+Alfin1 fragments. (C) GUS activity for each construct using the *Nicotiana* transient system for nitrate and chloride treated plants with fold induction shown above each bar. Experiments were performed in triplicate with standard errors shown.

Next, 4 bp deletions were made at four sites in the 109 bp fragment (SEQ ID NO:10) that correspond to potential regulatory motifs (i.e. predicted transcription factor binding sites based on the AthaMap analysis software (see the world wide web at athamap.de) (FIG. 15A). A deletion in the 5' HVH21 site (SEQ ID NO:5) reduced the nitrate response by 26% relative to the wildtype 109 bp fragment (SEQ ID NO:10) of NIA1-14e (FIG. 15C: –hvh21). A deletion in the Myb-1 site (–myb1) had little effect while a deletion in the Myb-2 (SEQ ID NO:7; SEQ ID NO:20) (–myb2) or Alfin1 (SEQ ID NO:8; SEQ ID NO:21) (–alfin) sites reduced the response by 100% and 75%, respectively. These results indicate that the Myb-2 and Alfin1 sites are critical for enhancer function while the 5' HVH21 (SEQ ID NO:5) site plays a contributing role.

If the above conclusion is correct, then a fragment containing these three sites should reconstruct full nitrate induction comparable to that of the 109 bp (SEQ ID NO:10) or 180 bp (SEQ ID NO:11) NIA1-14e fragments. First, a fragment containing only the Myb-2 and Alfin1 sites was tested (FIG. 15B: Myb2+Alfin1; (SEQ ID NO:14)); very little nitrate response was observed (FIG. 15C: +myb2+-alfin). When the HVH21 site (SEQ ID NO:13) was added to the Myb-2+Alfin1 fragment (FIG. 15C: +HVH21), activity was restored; however, the activity depended on the distance between the HVH21 sequence and the Myb-2+Alfin1 fragment. Spacers shorter than the native length gave reduced induction: a 7 bp spacer (FIG. 15C: 7 sp) restored only 53% of the nitrate induction, and a 16 bp spacer (FIG. 15C: 16 sp) restored only 43% of the induction compared with the wildtype 109 bp fragment (SEQ ID NO:10). Other spacers (23 and 26 bp) gave even less activity. However, a 44 bp spacer (FIG. 15C: 44 sp, the same length found in the native DNA), showed the highest level of induction (140% of the 109 bp fragment). These results show that the combination of the HVH21, Myb-2 and Alfin1 sites with sufficient spacing between the HVH21 and the Myb-2–Alfin1 sites is sufficient for full nitrate enhancer function.

Validation in Transgenic *Arabidopsis* Plants

Figure 16:
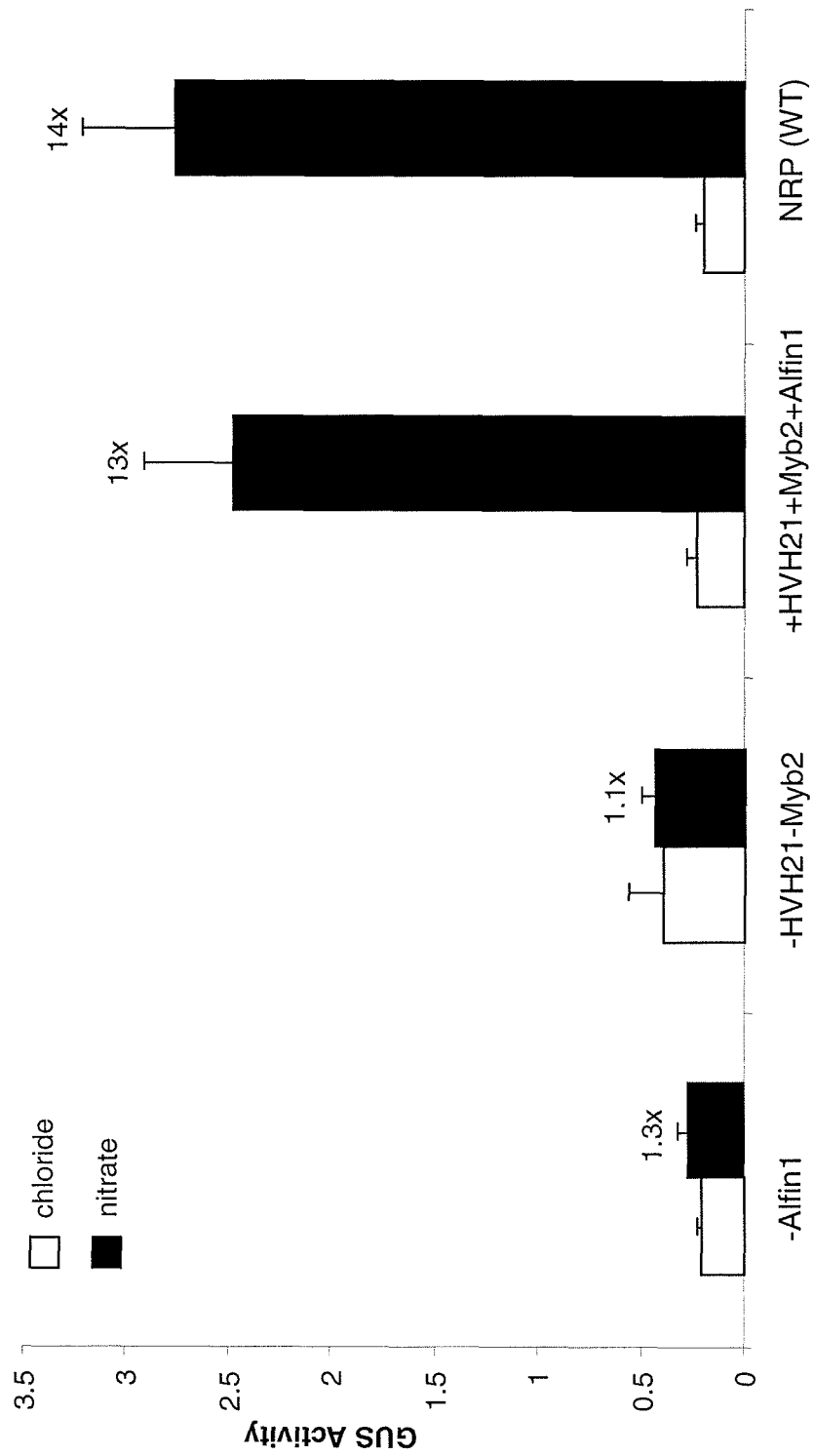
FIG. 16. Validation of promoter constructs in transgenic *Arabidopsis*. Transgenic seedlings grown on agarose plates with ammonium and no nitrate were transferred to plates containing 10 mM nitrate or 10 mM chloride for 24 h. GUS activity (nmol/(mg protein-hr)) was determined for three independent transgenic lines then averaged (error bars show standard error). Each GUS assay was performed in triplicate for each transgenic line. The fold of nitrate induction is indicated above each bar. Labels are as follows: −Alfin1: 4 bp deletion in Alfin1 site; −HVH21−Myb2: 4 bp deletions in HVH21 and Myb-2 sites; +HVH21+Myb2+Alfin1: HVH21 fragment fused to Myb-2+Alfin1 fragment with 44 bp spacer; NRP: tripartite promoter. The first three constructs used the 109 bp 3d3 fragment.

Several key constructs tested in the transient system described above were transformed and tested in transgenic *Arabidopsis* plants. The original tripartite NRP construct showed 14-fold induction (FIG. 16, NRP, see also FIG. 10). The Alfin1 single mutant showed almost no activity (FIG. 16: –Alfin1). The Myb-2 and HVH21 double mutant showed no activity (FIG. 16: –HVH21–Myb2). For the reconstructed fragment containing the HVH21 site fused to Myb-2+Alfin1 with a 44 bp spacer (same length as the native sequence), full induction was restored (FIG. 16: +HVH21+Myb2+Alfin1). Thus, the results in transgenic *Arabidopsis* plants validate the presence of three NEEs in the NIA1-14e fragment of the NIA1 promoter.

Analysis of the Nitrite Response for the 180 bp Enhancer

Nitrite also serves as a potent signal to rapidly induce and repress nitrate-regulated genes including NIA1 and NiR (Wang R et al., *Plant Physiol.*, 145: 1735-1745 (2007)). We tested transgenic plants containing various NRP constructs to determine if the NRP promoter responded to nitrite, and if a nitrite response was dependent on the same enhancer elements required for nitrate induction.

Figure 17:
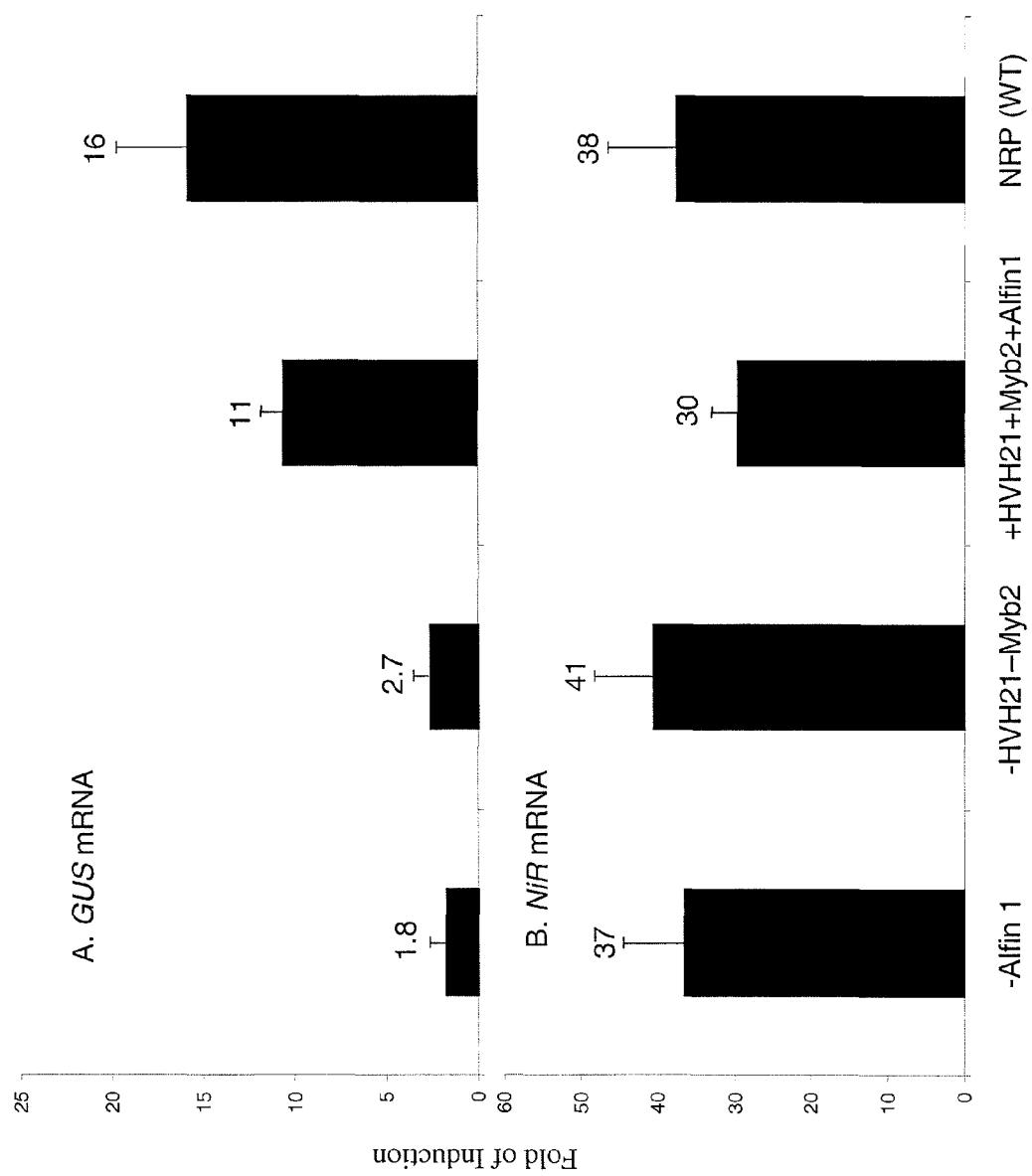
FIG. 17. Nitrite response of NRP-GUS constructs in transgenic plants. Plants were grown on vertical agarose plates with nitrate-free growth media containing 2.5 mM ammonium succinate for 7 d under continuous light. Plates were then flooded with 15 ml of fresh medium plus 1 mM $KNO_2$ or KCl for 30 min. Roots were collected at end of treatment for total RNA preparation. Messenger RNA levels of GUS (A) and NiR (B) were assayed by real-time quantitative PCR with clathrin (At4g24550) as the reference gene. Two independent transgenic lines for each construct were used. Experiments were in triplicates, and error bars show standard error.

NRP-GUS transgenic plants were grown with ammonium as the sole N source, treated with 1 mM $KNO_2$ (using 1 mM KCl as control) for 30 min, then GUS mRNA levels in roots were measured (FIG. 17). The NRP-GUS construct showed 16-fold induction by nitrite, which is similar to the level induced by nitrate. Nitrite inductions of modified NRP constructs with either the Alfin1 site or both the HVH21 and Myb-2 sites mutated were reduced 9-fold and 6-fold, respectively. The reconstructed enhancer fragment containing all three sites with a spacer of native length between the HVH21 and Myb-2 sites showed 11-fold induction by nitrite, almost as much as the original NRP promoter. For a control, mRNA levels for the endogenous NiR gene were determined, and they showed similar induction levels in all four sets of transgenics plants. These results show that the NRP construct is strongly induced by nitrite, and the same three enhancer elements needed for nitrate induction are also needed for nitrite induction.

Materials and Methods

Transgenic Lines

Transgenic *Arabidopsis* plants were produced by the floral dip procedure using 4-week-old plants and *Agrobacterium tumefaciens* cultures containing the appropriate constructs (Bechtold N et al., *Mol. Biol. Genet.*, 316: 1194-1199 (1993)). Seeds from treated plants were collected and screened for kanamycin resistance.

Growth and Treatment Conditions

For nitrate treatments of *Arabidopsis*, plants were grown for 10-14 d under 24 hr light on agarose plates with nitrate-free growth media containing 2.5 mM ammonium succinate as described (Wang R et al., *Plant Physiol.*, 132: 556-567 (2003); Wang R et al., *Plant Physiol.*, 136: 2512-2522 (2004)). Seedlings were transferred for 16 to 24 h to fresh growth media with either 10 mM $NH_4NO_3$ as the N-source (replacing ammonium succinate) or 10 mM KCl. Seedlings were then collected for GUS assay. Each GUS assay contained 25 seedlings, and was performed in triplicate for each transgenic line.

For the transient system, *Nicotiana benthamiana* seeds were germinated in soil then seedlings were transferred to perlite at the two to three-leaf stage. Plants were grown for three weeks at 25-27° C. with 16 hr light and irrigated with modified hydroponic solution containing ammonium and no nitrate (10 mM $KPO_4$, pH 6.5, 2.5 mM $(NH_4)_2SO_4$, 2 mM $MgSO_4$, 1 mM $CaCl_2$, 0.1 mM $FeNa_2EDTA$, and micronutrients (50 µm $H_3BO_3$, 12 µm $MnSO_4$, 1 µm $ZnCl_2$, 1 µm $CuSO_4$, and 0.2 µm $Na_2MoO_4$)) (Wang R et al., *Plant Physiol.*, 132: 556-567 (2003)). Plants were infiltrated with *Agrobacteria* and irrigated with 10 mM $KNO_3$ or KCl as described below.

Transient Expression Assays

All the constructs were transformed into *Agrobacterium tumefaciens* strains C1058. Individual *Agrobacteria* colonies, grown for 20 h in 5-ml Luria broth containing 50 µg/ml rifampicin, 25 µg/ml gentamycine, 5 µg/ml tetracycline, were used to inoculate a 50-ml culture (Luria broth, 20 µm acetosyringone, 10 mM MES, pH 5.7, 5 µg/ml tetracycline), which was grown for 16-20 h at 28° C. (Llave C et al., *Proc Natl Acad Sci USA*, 97: 13401-13406 (2000)). Bacteria were pelleted, resuspended in infiltration medium (10 mM $MgCl_2$, 10 mM MES, pH 5.7, 150 µM acetosyringone) to an $OD_{600}$ of 0.5, then incubated at room temperature for 3 h (Llave C et al., *Proc Natl Acad Sci USA*, 97: 13401-13406 (2000)).

After the initial 3 weeks of growth on nitrate-free hydroponic solution, *N. benthamiana* plants were irrigated with hydroponic solution containing either 10 mM KCl or 10 mM $KNO_3$ 30 min before infiltration. The third leaf form the top was then infiltrated with *Agrobacteria* using a 1-ml syringe (without needle) by injecting 0.2 ml of the *Agrobacteria* solution into leaf. Plants were again irrigated with hydroponic solution containing 10 mM KCl or $KNO_3$ 2-3 days after infiltration, then the third leaf from the top was collected for GUS assays 24 hr after the final irrigation.

Quantitative GUS Assays

For transgenic *Arabidopsis* plants, 25 seedlings were ground in liquid nitrogen, and soluble proteins were extracted with GUS buffer (100 mM $KPO_4$, pH 7.8, 2 mM EDTA, 5% glycerol, 2 mM DTT). GUS assays were performed as described (Beaud D et al., *Microbiology*, 151: 2323-2330 (2005)). Reactions were initiated by mixing 50 µl of protein extract with 120 µl of 1 mM p-nitrophenyl-β-D-glucuronide (PNPG) (Sigma-Aldrich). Reactions were incubated at 37° C. for 1-4 h (GUS activity stayed linear for up to 16 h) then stopped by adding 800 µl 125 mM $Na_2CO_3$. $OD_{415}$ was then measured with a spectrophotometer. Standard curves were made using p-nitrophenol (0-0.5 mM).

For the transient *Nicotiana* system, leaves were harvested and frozen in −80° C. 3-4 days post infiltration. Frozen leaf tissue (0.1 µm) was pulverized then suspended into 1 ml GUS extraction buffer (0.1 M $KPO_4$, pHv7.8, 2 mM EDTA, 5% glycerol, 2 mM dithiothreitol). Glucuronidase activity was assayed in a GUS assay buffer (50 mM Na $PO_4$, pH 7.0, 10 mM EDTA, 0.1% Triton X-100, 10 mM 2-mercaptoethanol and 1 mM p-nitrophenyl β-D-glucuronide) as described (Jefferson R A et al., *Proc Natl Acad Sci USA*, 83: 8447-8451 (1986)).

DNA Constructs

Promoter constructs were introduced into the HindIII and PstI sites of the binary vector pDW294, which contains a CaMV 35S minimal promoter upstream of the coding region for β-glucuronidase as described (Busch M A et al., *Science*, 285: 585-587 (1999)).

Transcription factor binding sites were predicted using AthaMap (see the world wide web at athamap.de). Sequence of the NIA1-NiR components of the NRP tripartite promoter is provided at Genbank as #GQ374175.

This example demonstrates that a 180 bp fragment in the NIA1 promoter has nitrate enhancer function and locates three cis-regulatory elements within the 180 bp fragment that account for the enhancer activity. These regulatory elements act synergistically to form a cis-regulatory module (as defined in (Priest H D et al., *Curr Opin Plant Biol.*, 12: 643-649 (2009))) that mediates nitrate induction. Together with the elements identified by Konishi et al., in the 43 bp fragment of NiR, (Konishi M, Yanagisawa S, *Plant J*, DOI: TPJ4239, 10.1111/j.1365-313X2010.04239.x (2010)), these sequence motifs provide the first insights into the identity of nitrate enhancer elements in plants.

The three regulatory elements in the 180 bp NIA1 fragment are candidate transcription factor binding sites. They were initially identified as potential binding sites by the AthaMap software. The first motif, a potential HVH21 site, contains a TGAC consensus sequence that binds homeodomain proteins of the knotted class 1 type (Krusell L et al., *FEBS Lett.*, 408: 25-29 (1997)). This site also overlaps with an E-box, which has a consensus sequence CANNTG and binds factors in the bHLH family of factors (Toledo-Ortiz G et al., *Plant Cell*, 15: 1749-1770 (2003)). The E-box element in the 180 bp fragment (CAAGTG) is very similar to the canonical E-box sequence: CACGTG. Interestingly, there are homeodomain factors that bind E-boxes (Aigner K et al., *FEBS Lett*, 581: 1617-1624 (2007)); thus, this site has the potential to bind either bHLH or homeodomain factors. The two Myb sites predicted by AthaMap correspond to motifs that contain the consensus sequence C-G/C-GTT-G/A, which was originally described as a site that binds GA-induced Myb proteins from barley (Gubler F et al., *Plant J*, 17: 1-9 (1999)). Even though the two GA-Myb sites have identical GTTG core sequences, the first one shows no activity while the second is essential. The Alfin1 site has a core consensus sequence of C/A-CAC, which was first shown to bind a novel zinc-finger protein in alfalfa (Bastola D R et al., *Plant Mol Biol*, 38: 1123-1135 (1998)).

One of the advances that made it possible to identify the three regulatory elements in the 180 bp NIA1 fragment was the inclusion of the 131 bp NiR fragment in the NRP construct. Even though the 180 bp fragment acted as a nitrate enhancer on its own (with only the 35S minimal promoter), its activity was increased almost 10-fold by the NiR fragment.

The NRP tripartite promoter described herein was also useful in a genetic screen to identify nitrate regulatory mutants, as described in Example 1 (Wang R et al., *Plant Physiol.*, 151: 472-478 (2009)). The transient expression system in *N. benthamiana* and the NRP tripartite construct described herein will facilitate identification of other nitrate enhancer fragments and elements. The transient system facilitates rapid analysis of nitrate responses for promoter constructs compared with several months needed for transgenic plants. The validation of the *N. benthamiana* results in *Arabidopsis* suggests that results from the transient system will be applicable to transgenic plants. The 35S minimal promoter alone does not appear to be sensitive enough to detect enhancer activity from these proximal regions. The 131 bp NiR fragment used in the NRP constructs provides a possible solution as it greatly increases the sensitivity of the system to the NIA1 upstream nitrate enhancers. If the 131 bp NiR fragment acts similarly for other nitrate enhancers, it will help locate other fragments and elements that the 35S minimal promoter alone would miss.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

INFORMAL SEQUENCE LISTING

Nia1_up_180bp sequence in artificial promoter: contains restriction
enzyme sites at 5' and 3' ends.
SEQ ID NO: 1 aagcttCGAAAATTCAAACAAGTGACAAAAATAATATTACGACCCGTCCCTTTGTTT

GGTTGCCCCGTTCGTGTATTTGCTTGGCCGTTGGTGTTCCCATGCGCCACTTAGCC

TCCAAAGTCTTCTCTCTAAACTCCTTTTTTATACCATAATCTCTGTTTAGTTTATAC

TTAATTGCGCTTTATCctgcag

NiR_up_130bp sequence in NRP artificial promoter:
contains RE site at 3' end.
SEQ ID NO: 2

TAAACACAATTTAAATAGTTTCAAATAAATTTAGAAAGAATAAAACAAATAGAA

ATCAGAAGGTGTCTGTTTCCTCCTCGCAACATACGATCAAAGAGAAACAACTTGA

CCCTTTACATTGCTCAAGAGCTtctaga 35S minimal promoter sequence:
SEQ ID NO: 3

GCAAGACCCTTCCTCTATATAAGGAAGTTCATTTCATTTGGAGAGGACACGCTGA

Cloning sites and 35S minimal promoter sequence:
SEQ ID NO: 4 ggatccggtaccGCAAGACCCTTCCTCTATATAAGGAAGTTCATTTCATTTGGAGAGGA

CACGCTGAgatccccgggtaggtcagtccctt

HVH21 site
SEQ ID NO: 5

CAAGTGAC

Sequence comprising HVH21
SEQ ID NO: 6

TCAAACAAGTGACAAAAATAATAT

Myb-2
SEQ ID NO: 7

TGGCCGT

Alfin1
SEQ ID NO: 8

ATGCGCC

Myb-2 + Alfin1
SEQ ID NO: 9

TGTATTTGCTTGGCCGTTGGTGTTCCCATGCGCCACTTA 109 by (3d3) fragment of 180 by NIA1 promoter fragment
SEQ ID NO: 10

TCGAAAATTCAAACAAGTGACAAAAATAATATTACGACCCGTCCCTTTGTTTGGT

TGCCCCGTTCGTGTATTTGCTTGGCCGTTGGTGTTCCCATGCGCCACTTAGCCT 180 by NIA1 promoter without RE sites.
SEQ ID NO: 11

CGAAAATTCAAACAAGTGACAAAAATAATATTACGACCCGTCCCTTTGTTTGGTT

GCCCCGTTCGTGTATTTGCTTGGCCGTTGGTGTTCCCATGCGCCACTTAGCCTCCA

AAGTCTTCTCTCTAAACTCCTTTTTTATACCATAATCTCTGTTTAGTTTATACTTAA

TTGCGCTTTATC 131 by NiR promoter.
SEQ ID NO: 12

TAAACACAATTTAAATAGTTTCAAATAAATTTAGAAAGAATAAAACAAATAGAA

ATCAGAAGGTGTCTGTTTCCTCCTCGCAACATACGATCAAAGAGAAACAACTTGA

CCCTTTACATTGCTCAAGAGCT

Sequence comprising HVH21 with additional T at 5' end.
SEQ ID NO: 13

TTCAAACAAGTGACAAAAATAATAT

Myb-2 + Alfin1 binding sites, sequence shifted 5'.

SEQ ID NO: 14

TATTTGCTTGGCCGTTGGTGTTCCCATGCGCCACTTAGCCT

NRP Promoter (#GQ374175)

SEQ ID NO: 15

CGAAAATTCAAACAAGTGACAAAAATAATATTACGACCCGTCCCTTTGTTTGGTT

GCCCCGTTCGTGTATTTGCTTGGCCGTTGGTGTTCCCATGCGCCACTTAGCCTCCA

AAGTCTTCTCTCTAAACTCCTTTTTTATACCATAATCTCTGTTTAGTTTATACTTAA

TTGCGCTTTATCCTGCAGTAAACACAATTTAAATAGTTTCAAATAAATTTAGAAA

GAATAAAACAAATAGAAATCAGAAGGTGTCTGTTTCCTCCTCGCAACATACGATC

AAAGAGAAACAACTTGACCCTTTACATTGCTCAAGAGCT

Arabidopsis nitrate transporter NRT1.1 (CHL1) partial CDS.

SEQ ID NO: 16

AAGGGTAAACAAAAGCTGCC

ACACACTGAACAATTCCGTTCATTAGATAAGGCAGCAATAAGG

Partial amino acid sequence of wild-type Arabidopsis
nitrate transporter NRT1.1 (CHL1).

SEQ ID NO: 17

Lys Gly Lys Gln Lys Leu Pro His Thr Glu Gln Phe Arg Ser Leu

Asp Lys Ala Ala Ile Arg

Mut21 (nrg1) Arabidopsis nitrate transporter NRT1.1 (CHL1) partial CDS.

SEQ ID NO: 18

AAGGGTAAACAAAAGCTGCCACACACTGAATAATTCCGTTCATTAGATAAGGCA

GCAATAAGG

Partial amino acid sequence of Mut21 (nrg1) Arabidopsis nitrate
transporter NRT1.1 (CHL1).

SEQ ID NO: 19

Lys Gly Lys Gln Lys Leu Pro His Thr Glu (Stop)

Myb-2 nitrate enhancer element (NEE) transcription factor binding site.

SEQ ID NO: 20

GGCCGTTG

Alfin1 nitrate enhancer element (NEE) transcription factor binding site.

SEQ ID NO: 21

CGCCACTTAG

Synthetic nitrate-responsive promoter (NRP) fusion of Arabidopsis
nitrate reductase (NIA1) distal promoter region, nitrite reductase
(NiR) promoter region and Cauliflower mosaic virus (CaMV) 35S
minimal promoter fragments: complete functional promoter.

SEQ ID NO: 22

CGAAAATTCAAACAAGTGACAAAAATAATATTACGACCCGTCCCTTTGTTTGGTT

GCCCCGTTCGTGTATTTGCTTGGCCGTTGGTGTTCCCATGCGCCACTTAGCCTCCA

AAGTCTTCTCTCTAAACTCCTTTTTTATACCATAATCTCTGTTTAGTTTATACTTAA

TTGCGCTTTATCCTGCAGTAAACACAATTTAAATAGTTTCAAATAAATTTAGAAA

GAATAAAACAAATAGAAATCAGAAGGTGTCTGTTTCCTCCTCGCAACATACGATC

AAAGAGAAACAACTTGACCCTTTACATTGCTCAAGAGCTTCTAGAGGATCCGGTA

CCGCAAGACCCTTCCTCTATATAAGGAAGTTCATTTCATTTGGAGAGGACACGCT

GAGATCCCCGGGTAGGTCAGTCCC

What is claimed is:

1. An expression cassette comprising a promoter operably linked to a heterologous polynucleotide, wherein the promoter comprises SEQ ID NO:2, SEQ ID NO:5, SEQ ID NO:7 and SEQ ID NO:8 linked to a minimal promoter sequence.

2. The expression cassette of claim 1, wherein the promoter comprises SEQ ID NO:6, SEQ ID NO:9, or both.

3. The expression cassette of claim 1, wherein the promoter comprises SEQ ID NO:6 and SEQ ID NO:9.

4. The expression cassette of claim 1, wherein the promoter comprises SEQ ID NO:6 and SEQ ID NO:9 linked by a spacer sequence, wherein the spacer sequence is between 5-200 nucleotides long.

5. The expression cassette of claim 1, wherein the promoter comprises a nucleotide sequence having at least 95% sequence identity to SEQ ID NO:1 across SEQ ID NO:1's entire length, linked to a minimal promoter sequence.

6. The expression cassette of claim 1, wherein the promoter comprises SEQ ID NO:13, SEQ ID NO:14, or both.

7. The expression cassette of claim 1, wherein the promoter comprises SEQ ID NO:13 and SEQ ID NO:14.

8. The expression cassette of claim 1, wherein the promoter comprises SEQ ID NO:13 and SEQ ID NO:14 linked by a spacer sequence, wherein the spacer sequence is between 5-200 nucleotides long.

9. The expression cassette of claim 1, wherein the promoter comprises a nucleotide sequence having at least 95% sequence identity to SEQ ID NO:11 across SEQ ID NO:11's entire length, linked to a minimal promoter sequence.

10. The expression cassette of claim 1, wherein the minimal promoter sequence comprises SEQ ID NO:3.

11. The expression cassette of claim 1, wherein the promoter comprises SEQ ID NO:1.

12. The expression cassette of claim 1, wherein the promoter comprises SEQ ID NO:1 and SEQ ID NO:2, wherein SEQ ID NO:1 is upstream of SEQ ID NO:2.

13. The expression cassette of claim 1, wherein the promoter comprises SEQ ID NO:11.

14. The expression cassette of claim 1, wherein the promoter comprises SEQ ID NO:12.

15. The expression cassette of claim 1, wherein the promoter comprises SEQ ID NO:11 and SEQ ID NO:12, wherein SEQ ID NO:11 is upstream of SEQ ID NO:12.

16. The expression cassette of claim 1, wherein the heterologous polynucleotide encodes a polypeptide.

17. The expression cassette of claim 1, wherein the heterologous polynucleotide codes for an siRNA or antisense RNA.

18. The expression cassette of claim 1, wherein the promoter is nitrate responsive when introduced into a plant.

19. A vector comprising the expression cassette of claim 1.

20. A plant, plant part, seed or plant cell comprising the expression cassette of claim 1.

21. A host plant, bacterial, yeast, fungi, insect, or non-human animal cell comprising the expression cassette of claim 1.

22. A method of introducing an expression cassette into a cell or plant, the method comprising introducing the expression cassette of claim 19 or the vector of claim 20 into a cell, plant cell or plant.

23. A method of inducing expression of the promoter in the plant of claim 20, the method comprising, contacting the plant with a synthetic exogenous nitrate source, thereby inducing expression of the promoter.

\* \* \* \* \*

SEQUENCE LISTING

<160> NUMBER OF SEQ ID NOS: 22

<210> SEQ ID NO 1
<211> LENGTH: 192
<212> TYPE: DNA
<213> ORGANISM: Artificial Sequence
<220> FEATURE:
<223> OTHER INFORMATION: synthetic nitrate-responsive enhancer,
      nitrate-regulated promoter (NRP), nitrate inducible promoter
      Nia1_up_180bp from Arabidopsis nitrate reductase (NIA1) distal
      promoter region containing restriction endonuclease sites, NIA1
      enhancer fragment

<400> SEQUENCE: 1
aagcttcgaa aattcaaaca agtgacaaaa ataatattac gacccgtccc tttgtttggt      60
tgccccgttc gtgtatttgc ttggccgttg gtgttcccat gcgccactta gcctccaaag     120
tcttctctct aaactccttt tttataccat aatctctgtt tagtttatac ttaattgcgc     180
tttatcctgc ag                                                         192

<210> SEQ ID NO 2
<211> LENGTH: 137
<212> TYPE: DNA
<213> ORGANISM: Artificial Sequence
<220> FEATURE:
<223> OTHER INFORMATION: synthetic nitrate-responsive enhancer,
      nitrate-regulated promoter (NRP), nitrate inducible promoter
      NiR_up_130bp from Arabidopsis nitrite reductase (NiR) promoter
      region containing restriction endonuclease site, NiR 3' fragment R

<400> SEQUENCE: 2
taaacacaat ttaaatagtt tcaaataaat ttagaaagaa taaacaaat agaaatcaga       60 aggtgtctgt ttcctcctcg caacatacga tcaaagagaa acaacttgac cctttacatt    120
gctcaagagc ttctaga                                                    137

<210> SEQ ID NO 3
<211> LENGTH: 55
<212> TYPE: DNA
<213> ORGANISM: Artificial Sequence
<220> FEATURE:
<223> OTHER INFORMATION: synthetic Cauliflower mosaic virus (CaMV) 35S
      minimal promoter fragment

<400> SEQUENCE: 3
gcaagaccct tcctctatat aaggaagttc atttcatttg gagaggacac gctga            55

<210> SEQ ID NO 4
<211> LENGTH: 91
<212> TYPE: DNA
<213> ORGANISM: Artificial Sequence
<220> FEATURE:
<223> OTHER INFORMATION: synthetic cloning sites and Cauliflower mosaic
      virus (CaMV) 35S minimal promoter fragment

<400> SEQUENCE: 4
ggatccggta ccgcaagacc cttcctctat ataaggaagt tcatttcatt tggagaggac       60
acgctgagat ccccgggtag gtcagtccct t                                     91

<210> SEQ ID NO 5
<211> LENGTH: 8
<212> TYPE: DNA
<213> ORGANISM: Artificial Sequence
<220> FEATURE:
<223> OTHER INFORMATION: synthetic cis-regulatory element HVH21 nitrate
      enhancer element (NEE) transcription factor binding site

<400> SEQUENCE: 5 caagtgac                                                                        8

<210> SEQ ID NO 6
<211> LENGTH: 24
<212> TYPE: DNA
<213> ORGANISM: Artificial Sequence
<220> FEATURE:
<223> OTHER INFORMATION: synthetic sequence comprising cis-regulatory
      element HVH21 nitrate enhancer element (NEE)
      transcription factor binding site

<400> SEQUENCE: 6
tcaaacaagt gacaaaaata atat                                                      24

<210> SEQ ID NO 7
<211> LENGTH: 7
<212> TYPE: DNA
<213> ORGANISM: Artificial Sequence
<220> FEATURE:
<223> OTHER INFORMATION: synthetic cis-regulatory element Myb-2 nitrate
      enhancer element (NEE) transcription factor
      binding site

<400> SEQUENCE: 7 tggccgt                                                                         7

<210> SEQ ID NO 8
<211> LENGTH: 7
<212> TYPE: DNA
<213> ORGANISM: Artificial Sequence
<220> FEATURE:
<223> OTHER INFORMATION: synthetic cis-regulatory element Alfin1 nitrate
      enhancer element (NEE) transcription factor
      binding site

<400> SEQUENCE: 8 atgcgcc                                                                         7

<210> SEQ ID NO 9
<211> LENGTH: 39
<212> TYPE: DNA
<213> ORGANISM: Artificial Sequence
<220> FEATURE:
<223> OTHER INFORMATION: synthetic cis-regulatory elements Myb2 + Alfin1
      nitrate enhancer elements (NEE) transcription
      factor binding sites

<400> SEQUENCE: 9
tgtatttgct tggccgttgg tgttcccatg cgccactta                                       39

<210> SEQ ID NO 10
<211> LENGTH: 109
<212> TYPE: DNA
<213> ORGANISM: Artificial Sequence
<220> FEATURE:
<223> OTHER INFORMATION: synthetic nitrate-responsive enhancer,
      nitrate-regulated promoter (NRP), nitrate inducible promoter
      NIA1-14e 109 bp fragment (3d3) from 5' end of Arabidopsis nitrate
      reductase (NIA1) distal promoter region

<400> SEQUENCE: 10
tcgaaaattc aaacaagtga caaaaataat attcgaccc gtcccttttgt ttggttgccc               60 cgttcgtgta tttgcttggc cgttggtgtt cccatgcgcc acttagcct                          109

<210> SEQ ID NO 11
<211> LENGTH: 180
<212> TYPE: DNA
<213> ORGANISM: Artificial Sequence
<220> FEATURE:
<223> OTHER INFORMATION: synthetic nitrate-responsive enhancer,
    nitrate-regulated promoter (NRP), nitrate inducible promoter
    Nia1_up_180bp from Arabidopsis nitrate reductase (NIA1) distal
    promoter region without restriction endonuclease sites, NIA1
    enhancer fragment

<400> SEQUENCE: 11
cgaaaattca aacaagtgac aaaaataata ttacgacccg tcccttttgtt tggttgcccc      60 gttcgtgtat ttgcttggcc gttggtgttc ccatgcgcca cttagcctcc aaagtcttct     120
ctctaaactc ctttttata ccataatctc tgtttagttt atacttaatt gcgctttatc      180

<210> SEQ ID NO 12
<211> LENGTH: 131
<212> TYPE: DNA
<213> ORGANISM: Artificial Sequence
<220> FEATURE:
<223> OTHER INFORMATION: synthetic nitrate-responsive enhancer,
    nitrate-regulated promoter (NRP), nitrate inducible promoter
    NiR_up_130bp from Arabidopsis nitrite reductase (NiR) promoter
    region without restriction endonuclease site, NiR 3' fragment R

<400> SEQUENCE: 12
taaacacaat ttaaatagtt tcaaataaat ttagaaagaa taaaacaaat agaaatcaga      60
aggtgtctgt ttcctcctcg caacatacga tcaaagagaa acaacttgac cctttacatt     120
gctcaagagc t                                                          131

<210> SEQ ID NO 13
<211> LENGTH: 25
<212> TYPE: DNA
<213> ORGANISM: Artificial Sequence
<220> FEATURE:
<223> OTHER INFORMATION: synthetic sequence comprising cis-regulatory
    element HVH21 nitrate enhancer element (NEE)
    transcription factor binding site

<400> SEQUENCE: 13
ttcaaacaag tgacaaaaat aatat                                            25

<210> SEQ ID NO 14
<211> LENGTH: 41
<212> TYPE: DNA
<213> ORGANISM: Artificial Sequence
<220> FEATURE:
<223> OTHER INFORMATION: synthetic cis-regulatory elements Myb-2 +
    Alfin1 nitrate enhancer elements (NEE) transcription factor
    binding sites

<400> SEQUENCE: 14
tatttgcttg gccgttggtg ttcccatgcg ccacttagcc t                          41

<210> SEQ ID NO 15
<211> LENGTH: 317
<212> TYPE: DNA
<213> ORGANISM: Artificial Sequence
<220> FEATURE:
<223> OTHER INFORMATION: synthetic nitrate-responsive promoter (NRP)
    fusion of Arabidopsis nitrate reductase (NIA1) distal promoter
    region, nitrite reductase (NiR) promoter region and Cauliflower
    mosaic virus (CaMV) 35S minimal promoter fragments

<400> SEQUENCE: 15

```
cgaaaattca aacaagtgac aaaaataata ttacgacccg tcccttttgtt tggttgcccc     60 gttcgtgtat ttgcttggcc gttggtgttc ccatgcgcca cttagcctcc aaagtcttct    120
ctctaaactc cttttttata ccataatctc tgtttagttt atacttaatt gcgctttatc    180
ctgcagtaaa cacaatttaa atagtttcaa ataaatttag aaagaataaa acaaatagaa    240
atcagaaggt gtctgtttcc tcctcgcaac atacgatcaa agagaaacaa cttgaccctt    300
tacattgctc aagagct                                                   317

<210> SEQ ID NO 16
<211> LENGTH: 63
<212> TYPE: DNA
<213> ORGANISM: Artificial Sequence
<220> FEATURE:
<223> OTHER INFORMATION: synthetic wild-type Arabidopsis nitrate
      transporter NRT1.1 (CHL1) partial CDS

<400> SEQUENCE: 16
aagggtaaac aaaagctgcc acacactgaa caattccgtt cattagataa ggcagcaata     60
agg                                                                   63

<210> SEQ ID NO 17
<211> LENGTH: 21
<212> TYPE: PRT
<213> ORGANISM: Artificial Sequence
<220> FEATURE:
<223> OTHER INFORMATION: synthetic partial wild-type Arabidopsis nitrate
      transporter NRT1.1 (CHL1)

<400> SEQUENCE: 17

Lys Gly Lys Gln Lys Leu Pro His Thr Glu Gln Phe Arg Ser Leu Asp
  1               5                  10                  15

Lys Ala Ala Ile Arg
             20

<210> SEQ ID NO 18
<211> LENGTH: 63
<212> TYPE: DNA
<213> ORGANISM: Artificial Sequence
<220> FEATURE:
<223> OTHER INFORMATION: synthetic Mut21 (nrg1) Arabidopsis nitrate
      transporter NRT1.1 (CHL1) partial CDS

<400> SEQUENCE: 18
aagggtaaac aaaagctgcc acacactgaa taattccgtt cattagataa ggcagcaata     60
agg                                                                   63

<210> SEQ ID NO 19
<211> LENGTH: 10
<212> TYPE: PRT
<213> ORGANISM: Artificial Sequence
<220> FEATURE:
<223> OTHER INFORMATION: synthetic partial Mut21 (nrg1) Arabidopsis
      nitrate transporter NRT1.1 (CHL1)

<400> SEQUENCE: 19

Lys Gly Lys Gln Lys Leu Pro His Thr Glu
  1               5                  10

<210> SEQ ID NO 20
<211> LENGTH: 8
<212> TYPE: DNA
<213> ORGANISM: Artificial Sequence
```

```
<220> FEATURE:
<223> OTHER INFORMATION: synthetic cis-regulatory element Myb-2 nitrate
      enhancer element (NEE) transcription factor
      binding site

<400> SEQUENCE: 20 ggccgttg                                                                    8

<210> SEQ ID NO 21
<211> LENGTH: 10
<212> TYPE: DNA
<213> ORGANISM: Artificial Sequence
<220> FEATURE:
<223> OTHER INFORMATION: synthetic cis-regulatory element Alfin1 nitrate
      enhancer element (NEE) transcription factor
      binding site

<400> SEQUENCE: 21
cgccacttag                                                                 10

<210> SEQ ID NO 22
<211> LENGTH: 412
<212> TYPE: DNA
<213> ORGANISM: Artificial Sequence
<220> FEATURE:
<223> OTHER INFORMATION: synthetic nitrate-responsive promoter (NRP)
      fusion of Arabidopsis nitrate reductase (NIA1) distal promoter
      region, nitrite reductase (NiR) promoter region and Cauliflower
      mosaic virus (CaMV) 35S minimal promoter fragments complete
      functional promoter

<400> SEQUENCE: 22
cgaaaattca aacaagtgac aaaaataata ttacgacccg tcccttttgtt tggttgcccc           60 gttcgtgtat ttgcttggcc gttggtgttc ccatgcgcca cttagcctcc aaagtcttct          120
ctctaaactc ctttttata  ccataatctc tgtttagttt atacttaatt gcgctttatc          180
ctgcagtaaa cacaatttaa atagtttcaa ataaatttag aaagaataaa acaaatagaa          240
atcagaaggt gtctgtttcc tcctcgcaac atacgatcaa agagaaacaa cttgaccctt          300
tacattgctc aagagcttct agaggatccg gtaccgcaag acccttcctc tatataagga          360
agttcatttc atttggagag gacacgctga gatccccggg taggtcagtc cc                  412
```